(12) United States Patent
Green et al.

(10) Patent No.: US 7,118,756 B2
(45) Date of Patent: Oct. 10, 2006

(54) RECOMBINANT PROTECTIVE PROTEIN FROM STREPTOCOCCUS PNEUMONIAE

(75) Inventors: Bruce A. Green, Pittsford, NY (US); Amy W. Masi, Caledonia, NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/433,385

(22) PCT Filed: Dec. 28, 2001

(86) PCT No.: PCT/US01/49650

§ 371 (c)(1),
(2), (4) Date: May 29, 2003

(87) PCT Pub. No.: WO02/053761

PCT Pub. Date: Jul. 11, 2002

(65) Prior Publication Data

US 2004/0052816 A1    Mar. 18, 2004

Related U.S. Application Data

(60) Provisional application No. 60/258,841, filed on Dec. 28, 2000.

(51) Int. Cl.
*A61K 39/09* (2006.01)
*A61K 39/02* (2006.01)
*A61K 39/00* (2006.01)
*A61K 38/00* (2006.01)
*C07K 1/00* (2006.01)

(52) U.S. Cl. .............. 424/244.1; 424/234.1; 424/190.1; 424/184.1; 530/350; 530/825; 514/2

(58) Field of Classification Search .......... 424/234.1, 424/244.1, 190.1, 93.44, 184.1; 514/2; 530/350, 530/300, 825
See application file for complete search history.

(56) References Cited

U.S. PATENT DOCUMENTS

| | | | | |
|---|---|---|---|---|
| 4,425,330 A | * | 1/1984 | Norcross et al. | 424/203.1 |
| 5,266,477 A | * | 11/1993 | Howard et al. | 435/336 |
| 6,291,654 B1 | * | 9/2001 | Hostetter et al. | 530/413 |
| 6,699,703 B1 | * | 3/2004 | Doucette-Stamm et al. | 435/252.3 |

FOREIGN PATENT DOCUMENTS

WO    WO 98/18931 A1    5/1998
WO    WO 99/15675    *    4/1999

OTHER PUBLICATIONS

Harlow et al. In: Antibodies: A laboratory Manual. Cold Sprting Harbor Laboratory, Chapter 5, p. 76, 1988.*
Houghton et al. Vaccines86, Cold Spring Harbor Laboratory, p. 21-25, 1986.*
Conte, et al., "Iron Availability Affects Entry of Listeria monocytogenes into the Enterocytelike Cell Line Caco-2," Infection and Immunity, Sep. 1996, p. 3925-3929.
Gray-Owen, et al., "Identification and Characterization of Genes Encoding the Human Transferrin-Binding Proteins from *Haemophilus influenzae*," Infection and Immunity, Apr. 1995, p. 1201-1210.
Luke, et al., "Use of an Isogenic Mutant Constructed in *Moraxella catarrhalis* To Identify a Protective Epitope of Outer Membrane Protein B1 Defined by Monoclonal Antibody 11C6," Infection and Immunity, Feb. 1999, p. 681-687.
Pettersson, et al., "Molecular Characterization of the 98-Kilodalton Iron-Regulated Outer Membrane Protein of Neisseria meningitidis," Infection and Immunity, Nov. 1993, p. 4724-4733.
Pikis, et al., "A Conservative Amino Acid Mutation in the Chromosome-Encoded Dihydrofolate Reductase Confers Trimethoprim Resistance in *Streptococcus pneumoniae*," The Journal of Infectious Diseases, 1998; 178:700-6.
Morrison, et al., "Isolation and Characterization of Three New Classes of Transformation-Deficient Mutants of *Streptococcus pneumoniae* That Are Defective in DNA Transport and Genetic Recombination," Journal of Bacteriology, Oct. 1983, p. 281-290.
Henriksen, et al., "Vaccination with Protein-Conjugated and Native Type 3 Capsular Polysaccharide in and Ethanol-Fed Rat Model of Pneumococcal Pneumonia," Alcohol Clin. Exp. Res., vol. 21, No. 9, 1997; p. 1630-1637.
Gray, "Opsonophagocidal Activity in Sera From Infants and Children Immunized With Haemophilus influenzae Type b Conjugate Vaccine (Meningococcal Protein Conjugate)," Pediatrics Conjugate Vaccines Supplement, 1990, p. 694-697.
H. Tettelin, "Complete Genome Sequence of a Virulent Isolate of *Streptococcus pneumoniae*" Science, Jul. 2001, vol. 293, 498-506.

* cited by examiner

*Primary Examiner*—S. Devi
(74) *Attorney, Agent, or Firm*—Carol E. Rozek; Bill T. Brazil

(57) ABSTRACT

The present invention discloses amino acid sequences and nucleic acid sequences relating to a *Streptococcus Pneumoniae* surface associated Pneumo Protective Protein (PPP) having a molecular weight of about 20 kilo Daltons (kDa). The PPP exhibits the ability to reduce colonization of pneumococcal bacteria. Thus the present invention also pertains to compositions for the treatment and prophylaxis of infection or inflammation associated with bacterial infection.

9 Claims, 6 Drawing Sheets

1  Standards
2  Fraction #8
3  Fraction #9
4  Fraction #10
5  Fraction #11
6  Fraction #12
7  Fraction #13
8  Fraction #14
9  Fraction #15
10 Fraction #16

FIG. 6A

```
                          1                                                    50
PPP1CP1200    (1)    MAVELKKEAVKDVTSLTKAAPVALAKTKEVLNQAVADLYVAHVALHQV
PPP1TYPE1     (1)    MAVELKKEAVKDVTSLTKAAPVALAKTKEVLNQAVADLYVAHVALHQV
PPP1TYPE14    (1)    MAVELKKEAVKDVTSLTKAAPVALAKTKEVLNQAVADLYVAHVALHQV
PPP1TYPE18    (1)    MAVELKKEAVKDVTSLTKAAPVALAKTKEVLNQAVADLYVAHVALHQV
PPP1TYPE23    (1)    ---AVELKKEAVKDVTSLTKAAPVALAKTKEVLNQAVADLYVAHVALHQV
PPP1TYPE3     (1)    MAVELKKEAVKDVTSLTKAAPVALAKTKEVLNQAVADLHVAHVALHQV
PPP1TYPE4     (1)    MAVELKKEAVKDVTSLTKAAPVALAKTKEVLNQAVADLYVAHVALHQV
PPP1TYPE5     (1)    MAVELKKEAVKDVTSLTKAAPVALAKTKEVLNQAVADLYVAHVALHQV
PPP1TYPE6B    (1)    MAVELKKEAVKDVTSLTKAAPVALAKTKEVLNQAVADLYVAHVALHQV
PPP1TYPE7     (1)    MAVELKKEAAKDVARLTKAAPVALAKTKEVLNQAVADLYVAHVALHQV
PPP1TYPE9     (1)    --MAVELKKEAAKDVARLTKAAPVALAKTKEVLNQAVADLYVAHVALHQV
Consensus     (1)    MAVELKKEAVKDVTSLTKAAPVALAKTKEVLNQAVADLYVAHVALHQV 51                                                   100
PPP1CP1200   (51)    HWYMHGRGFLVWHPKMDEYMEALDGQLDEISERLITLGGSPFSTLTEFLQ
PPP1TYPE1    (51)    HWYMHGRGFLVWHPKMDEYMEALDGQLDEISERLITLGGSPFSTLTEFLQ
PPP1TYPE14   (51)    HWYMHGRGFLVWHPKMDEYMEALDGQLDEISERLITLGGSPFSTLTEFLQ
PPP1TYPE18   (51)    HWYMHGRGFLVWHPKMDEYMEALDGQLDEISERLITLGGSPFSTLTEFLQ
PPP1TYPE23   (48)    HWYMHGRGFLVWHPKMDEYMEALDGQLDETSERLITLGGSPFSTLTEFLQ
PPP1TYPE3    (51)    HWYMHGRGFLVWHPKMDEYMEALDGQLDEISERLITLGGSPFSTLTEFLQ
PPP1TYPE4    (51)    HWYMHGRGFLVWHPKMDEYMEALDGQLDEISERLITLGGSPFSTLTEFLQ
PPP1TYPE5    (51)    HWYMHGRGFLVWHPKMDEYMEALDGQLDEISERLITLGGSPFSTLTEFLQ
PPP1TYPE6B   (51)    HWYMHGRGFLVWHPKMDEYMEALDGQLDEISERLITLGGSPFSTLTEFLQ
PPP1TYPE7    (51)    HWYMHGRGFLVWHPKMDEYMEALDGHLDEISERLITLGGSPFSTLTEFLQ
PPP1TYPE9    (49)    HWYMHGRGFLVWHPKMDEYMEALDGQLDEISERLITLGGSPFSTLTEFLQ
Consensus    (51)    HWYMHGRGFLVWHPKMDEYMEALDGQLDEISERLITLGGSPFSTLTEFLQ
```

FIG. 6B

```
               101                                                    150
PPP1CP1200  (101) NSEIEEEAGEYRNVEESLERVLVIYRYLSELFQKGLDVTDEEGDDVTNGI
PPP1TYPE1   (101) NSEIEEEAGEYRNVEESLERVLVIYRYLSELFQKGLDVTDEEGDDVTNGI
PPP1TYPE14  (101) NSEIEEEAGEYRNVEESLERVLVIYRYLSELFQKGLDVTDEEGDDVTNGI
PPP1TYPE18  (101) NSEIEEEAGEYRNVEESLERVLVIYRYLSELFQKGLDVTDEEGDDVTNGI
PPP1TYPE23   (98) NSEIEEEAGEYRNVEESLERVLVIYRYLSELFQKDLDVTDEEGDDVTNGI
PPP1TYPE3   (101) NSEIEEEAGEYRNVEESLERVLVIYRYLSELFQKGLDVTDEEGDDVTNDI
PPP1TYPE4   (101) NSEIEEEAGEYRNVEESLERVLVIYRYLSELFQKGLDVTDEEGDDVTNDI
PPP1TYPE5   (101) NSEIEEEAGEYRNVEESLERVLVIYRYLSELFQKGLDVTDEEGDDVTNGI
PPP1TYPE6B  (101) NSEIEEEAGEYRNVEESLERVLVIYRYLSELFQKGLDVTDEEGDDVTNGI
PPP1TYPE7   (101) NSEIEEEAGEYRNVEESLERVLVIYRYLSELFQKGLDVTDEEGDDVTNDI
PPP1TYPE9    (99) NSEIEEEAGEYRNVEESLERVLAIYRYLITLFQKALDVTDEEGDDVTNDI
Consensus   (101) NSEIEEEAGEYRNVEESLERVLVIYRYLSELFQKGLDVTDEEGDDVTNGI 151                                     178
PPP1CP1200  (151) FVGAKTETDKTIWMLAAELGQAPGLVDP  (SEQ ID NO: 21)
PPP1TYPE1   (151) FAGAKTETDKTIWMLAAELGQAPGLVDP  (SEQ ID NO: 10)
PPP1TYPE14  (151) FAGAKTETDKTIWMLAAELGQAPGLVDP  (SEQ ID NO: 11)
PPP1TYPE18  (151) FEGAKTETDKTIWMLAAELGQAPGLVDP  (SEQ ID NO: 12)
PPP1TYPE23  (148) FAGAKTETDKTIWMLAAELGQAPGLVDP  (SEQ ID NO: 13)
PPP1TYPE3   (151) FVGAKTETDKTIWMLAAELGQAPGLVDP  (SEQ ID NO: 14)
PPP1TYPE4   (151) FAGAKTETDKTIWMLAAELGQAPGLVDP  (SEQ ID NO: 15)
PPP1TYPE5   (151) FVGAKTETDKTIWMLAAELGQAPGLVDP  (SEQ ID NO: 16)
PPP1TYPE6B  (151) FAGAKTETDKTIWMLAAELGQAPGLVDP  (SEQ ID NO: 17)
PPP1TYPE7   (151) FAGAKTETDKTIWMLAAELGQAPGLVDP  (SEQ ID NO: 18)
PPP1TYPE9   (149) FVGAKAELEKTVWMLAAELGQAPGLVDP  (SEQ ID NO: 19)
Consensus   (151) FAGAKTETDKTIWMLAAELGQAPGLVDP  (SEQ ID NO: 20)
```

RECOMBINANT PROTECTIVE PROTEIN FROM *STREPTOCOCCUS PNEUMONIAE*

PRIORITY

This is the U.S. national phase application under 35 U.S.C. §371 of International Patent Application Ser. No. PCT/US01/49650, filed Dec. 28, 2001 and published in English on Jul. 11, 2002 under International Publication No. 02/053761, and also claims priority under 35 U.S.C. §119(e) from U.S. Provisional Patent Application Ser. No. 60/258,841, filed Dec. 28, 2000, which are both hereby incorporated by reference in their entirety.

FIELD OF THE INVENTION

The present invention provides amino acid sequences and nucleic acid sequences relating to a protein of *Streptococcus pneumoniae* having a molecular weight of 20 kilo Daltons (kDa). The present invention also pertains to compositions for the treatment and prophylaxis of infection or inflammation associated with bacterial infection.

BACKGROUND OF THE INVENTION

The middle ear is a sterile, air-filled cavity separated from the outer ear by the eardrum. Attached to the eardrum are three ear bones that vibrate when sound waves strike the eardrum. Vibrations are transmitted to the inner ear, which generates nerve impulses that are sent to the brain. Air may enter the middle ear through the Eustachian tube, which opens in the walls of the nasopharynx.

The nasopharynx is located posterior to the nasal cavities. The nasopharynx is lined by the respiratory epithelium and stratified squamous epithelium. Beneath the respiratory epithelium, the abundant mucosa-associated lymphoid tissue (MALT) forms the nasopharyngeal tonsil (adenoids).

Bacterial infection or inflammation of the middle ear is mainly observed in children. Due to the isolation of the middle ear, it is suggested that development of middle ear infections requires the involvement of the nasopharynx and Eustachian tube. Infections with *Streptococcus pneumoniae* (*S. pneumoniae*) are one of the major causes of middle ear infections, as well as bacteremia, meningitis, and fatal pneumonia worldwide (Butler, J. C., et al., American Journal of Medicine, 1999, 107:69S–76S). The rapid emergence of multi-drug resistant pneumococcal strains throughout the world has led to increased emphasis on prevention of pneumococcal infections by vaccination (Goldstein and Garau, Lancet, 1997, 350:233–4).

Protein antigens of *S. pneumoniae* have been evaluated for protective efficacy in animal models of pneumococcal infection. Some of the most commonly studied vaccine candidates include the the PspA proteins, PsaA lipoprotein, and the CbpA protein. Numerous studies have shown that PspA protein is a virulence factor (Crain, M. J., et al., Infect Immun, 1990, 58:3293–9; McDaniel, L. S., et al., J Exp Med,1984, 160:386–97), but is antigenically variable among pneumococcal strains. Additionally, a recent study has indicated that some antigenically conserved regions of a recombinant PspA variant may elicit cross-reactive antibodies in human adults (Nabors, G. S., et al., Vaccine, 2000, 18:1743–1754). PsaA, a 37 kDa lipoprotein with similarity to other Gram-positive adhesins, is involved in manganese transport in pneumococci (Dintilhac, A., et al., Molecular Microbiology, 1997, 25(4):727–739; Sampson, J. S., et al., Infect Immun, 1994, 62:319–24.) and has been shown to be protective in mouse models of systemic disease (Talkington, D. F., et al., Microb Pathog, 1996. 21:17–22). The surface exposed choline binding protein, CbpA, is antigenically conserved and also is protective in mouse models of pneumococcal disease (Rosenow, C., et al. Molecular Microbiology, 1997, 25:819–29). Since nasopharyngeal colonization is a prerequisite for otic disease, intranasal immunization of mice with pneumococcal proteins and appropriate mucosal adjuvants has been used to enhance the mucosal antibody response and thus, the effectiveness of protein vaccine candidates (Briles, D. E., et al., Infect Immun, 2000, 68:796–800; Yamamoto, M., et al., A. J Immunol, 1998, 161:4115–21).

The currently available 23-valent pneumococcal capsular polysaccharide vaccine is not effective in children of less than 2 years of age or in immunocompromised patients, two of the major populations at risk from pneumococcal infection (Douglas, R. M., et al., Journal of Infectious Diseases, 1983, 148:131–137). A 7-valent pneumococcal polysaccharide-protein conjugate vaccine, was shown to be highly effective in infants and children against systemic pneumococcal disease caused by the vaccine serotypes and against cross-reactive capsular serotypes (Shinefield and Black, Pediatr Infect Dis J, 2000, 19:394–7). The seven capsular types cover greater than 80% of the disease isolates in the United States, but only 57–60% of disease isolates in other areas of the world (Hausdorff, W. P., et al., Clinical Infectious Diseases, 2000, 30:100–21). Therefore, there is an immediate need for a vaccine to cover most or all of the disease causing serotypes of pneumococci.

Iron is an essential element for colonization and infection by many pathogenic bacteria. Prevention of the acquisition process should result in a reduction of colonization and a lower disease potential. Iron acquisition complexes in successful pathogens such as, but not limited to, *N. gonorrheae*, *N. meningitidis*, *M. catarrhalis*, and *H. influenzae* have been evaluated for their vaccine potential by other laboratories (Conte, M. P, et al., Infection and Immunity, 1999, 64:3925; Gray-Owens, S. D., et al. Infection and Immunity, 1995, 64:1201; Luke N. R. et al., Infection and Immunity, 1999, 67:681; Pettersson, A, et al., Infection and Immunity, 1993, 61:4724). Thus, isolation of the structures responsible for iron acquisition could lead to vaccine candidates.

SUMMARY OF THE INVENTION

The present invention contemplates an isolated *S. pneumoniae* surface associated Pneumo Protective Protein (PPP) having a molecular weight of about 20 kilo Daltons (kDa), where the molecular weight is determined using a 10–20% SDS-PAGE gel, or a fragment thereof; the PPP having the ability to reduce colonization of pneumococcal bacteria.

The present invention contemplates a recombinant *S. pneumoniae* surface associated PPP having a molecular weight of about 20 kDa, where the molecular weight is determined using a 10–20% SDS-PAGE gel, or a fragment thereof; the PPP having the ability to reduce colonization of pneumococcal bacteria.

The present invention contemplates a recombinant *S. pneumoniae* surface associated PPP having a molecular weight of about 20 kDa, where the molecular weight is determined using a 10–20% SDS-PAGE gel, or a fragment thereof; the PPP having the ability to reduce colonization of pneumococcal bacteria; where the PPP has an isoelectric point of about 4.587.

The present invention contemplates a recombinant *S. pneumoniae* surface associated PPP having a molecular weight of about 20 kDa, where the molecular weight is determined using a 10–20% SDS-PAGE gel, or a fragment thereof; the PPP having the ability to reduce colonization of pneumococcal bacteria; where the PPP has an isoelectric point of about 4.587 and a charge of about −14.214 at pH 7.

The present invention also contemplates an isolated S. pneumoniae surface associated PPP having a molecular weight of about 20 kDa, where the molecular weight is determined using a 10–20% SDS-PAGE gel, or a fragment thereof; where the PPP has an amino acid sequence as depicted in SEQ ID NO: 5, or a fragment thereof; the PPP having the ability to reduce colonization of pneumococcal bacteria.

The present invention also contemplates a nucleic acid sequence encoding an isolated S. pneumoniae surface associated PPP having a molecular weight of about 20 kDa, where the molecular weight is determined using a 10–20% SDS-PAGE gel, or a fragment thereof; where the nucleic acid sequence has a sequence as depicted in SEQ ID NO: 4, or a fragment thereof; the PPP having the ability to reduce colonization of pneumococcal bacteria.

The present invention also contemplates a cDNA encoding an isolated S. pneumoniae surface associated PPP having a molecular weight of about 20 kDa, where the molecular weight is determined using a 10–20% SDS-PAGE gel, or a fragment thereof; where the nucleic acid sequence has a sequence as depicted in SEQ ID NO: 4, or a fragment thereof; the PPP having the ability to reduce colonization of pneumococcal bacteria.

The present invention contemplates an expression vector comprising a nucleic acid sequence encoding an isolated S. pneumoniae surface associated PPP having a molecular weight of about 20 kDa, where the molecular weight is determined using a 10–20% SDS-PAGE gel, or a fragment thereof; the PPP having the ability to reduce colonization of pneumococcal bacteria, where the sequence is operatively associated with an expression control sequence.

The present invention also contemplates a vector comprising a nucleic acid sequence encoding an isolated S. pneumoniae surface associated PPP having a molecular weight of about 20 kDa, where the molecular weight is determined using a 10–20% SDS-PAGE gel, or a fragment thereof; the PPP having the ability to reduce colonization of pneumococcal bacteria, where the sequence is operatively associated with an expression control sequence, and where the PPP has an isoelectric point of about 4.587.

The present invention further contemplates a vector comprising a nucleic acid sequence encoding an isolated S. pneumoniae surface associated PPP having a molecular weight of about 20 kDa, where the molecular weight is determined using a 10–20% SDS-PAGE gel, or a fragment thereof; the PPP having the ability to reduce colonization of pneumococcal bacteria, where the sequence is operatively associated with an expression control sequence, and where the PPP has an isoelectric point of about 4.587 and a charge of about −14.214 at pH 7.

The present invention also contemplates an expression vector comprising a nucleic acid sequence encoding a an isolated S. pneumoniae surface associated PPP having a molecular weight of about 20 kDa, where the molecular weight is determined using a 10–20% SDS-PAGE gel, or a fragment thereof; where the PPP has an amino acid sequence as depicted in SEQ ID NO: 5, or a fragment thereof; and where the nucleic acid sequence is operatively associated with an expression control sequence.

The present invention also contemplates an expression vector comprising a nucleic acid sequence encoding a an isolated S. pneumoniae surface associated PPP having a molecular weight of about 20 kDa, where the molecular weight is determined using a 10–20% SDS-PAGE gel, or a fragment thereof; where the PPP has an amino acid sequence as depicted in SEQ ID NO: 5, or a fragment thereof; where the amino acid sequence is encoded by the nucleic acid sequence as depicted in SEQ ID NO: 4, or a fragment thereof; and where the nucleic acid sequence is operatively associated with an expression control sequence.

The present invention contemplates a host cell transfected with an expression vector comprising a nucleic acid sequence encoding an isolated S. pneumoniae surface associated PPP having a molecular weight of about 20 kDa, where the molecular weight is determined using a 10–20% SDS-PAGE gel, or a fragment thereof; the PPP having the ability to reduce colonization of pneumococcal bacteria; where the sequence is operatively associated with an expression control sequence.

The present invention further contemplates a host cell transfected with a vector comprising a nucleic acid sequence encoding an isolated S. pneumoniae surface associated PPP having a molecular weight of about 20 kDa, where the molecular weight is determined using a 10–20% SDS-PAGE gel, or a fragment thereof; where the PPP has an amino acid sequence as depicted in SEQ ID NO: 5, or a fragment thereof; the PPP having the ability to reduce colonization of pneumococcal bacteria; where the sequence is operatively associated with an expression control sequence.

The present invention also contemplates a method for producing recombinant PPP, which method comprises isolating the PPP produced by a host cell transfected with an expression vector and cultured under conditions that provide for expression of the PPP by the vector, where the vector comprises a nucleic acid sequence encoding an isolated S. pneumoniae surface associated PPP having a molecular weight of about 20 kDa, where the molecular weight is determined using a 10–20% SDS-PAGE gel, or a fragment thereof; the PPP having the ability to reduce colonization of pneumococcal bacteria; where the sequence is operatively associated with an expression control sequence.

The present invention also contemplates a method for producing recombinant PPP, which method comprises isolating the PPP produced by host cell transfected with a vector and cultured under conditions that provide for expression of the PPP by the vector, where the vector comprises a nucleic acid sequence encoding an isolated S. pneumoniae surface associated PPP having a molecular weight of about 20 kDa, where the molecular weight is determined using a 10–20% SDS-PAGE gel, or a fragment thereof where the PPP has an amino acid sequence as depicted in SEQ ID NO: 5, or a fragment thereof; the PPP having the ability to reduce colonization of pneumococcal bacteria, where the sequence is operatively associated with an expression control sequence.

The present invention also contemplates a composition comprising (1) an isolated S. pneumoniae surface associated PPP having a molecular weight of about 20 kDa, where the molecular weight is determined using a 10–20% SDS-PAGE gel, or a fragment thereof; the PPP having the ability to reduce colonization of pneumococcal bacteria; and (2) a pharmaceutically acceptable carrier.

The present invention also contemplates a composition comprising (1) an isolated S. pneumoniae surface associated PPP having a molecular weight of about 20 kDa, where the molecular weight is determined using a 10–20% SDS-PAGE gel, or a fragment thereof; the PPP having the ability to reduce colonization of pneumococcal bacteria, and which PPP has an amino acid sequence as depicted in SEQ ID NO: 5, or a fragment thereof; and (2) a pharmaceutically acceptable carrier.

The present invention contemplates a composition comprising (1) a nucleic acid sequence encoding an isolated *S. pneumoniae* surface associated PPP having a molecular weight of about 20 kDa, where the molecular weight is determined using a 10–20% SDS-PAGE gel, or a fragment thereof; the PPP having the ability to reduce colonization of pneumococcal bacteria, where the nucleic acid sequence has a sequence as depicted in SEQ ID NO: 4, or a fragment thereof; and (2) a pharmaceutically acceptable carrier.

The present invention contemplates a composition comprising (1) an expression vector comprising a nucleic acid sequence encoding an isolated *S. pneumoniae* surface associated PPP having a molecular weight of about 20 kDa, where the molecular weight is determined using a 10–20% SDS-PAGE gel, or a fragment thereof; the PPP having the ability to reduce colonization of pneumococcal bacteria, where the sequence is operatively associated with an expression control sequence; and (2) a pharmaceutically acceptable carrier.

The present invention also contemplates a composition comprising (1) an expression vector comprising a nucleic acid sequence encoding a an isolated *S. pneumoniae* surface associated PPP having a molecular weight of about 20 kDa, where the molecular weight is determined using a 10–20% SDS-PAGE gel, or a fragment thereof; where the PPP has an amino acid sequence as depicted in SEQ ID NO: 5, or a fragment thereof, and where the nucleic acid sequence is operatively associated with an expression control sequence; and (2) a pharmaceutically acceptable carrier.

The present invention also contemplates a composition comprising (1) a host cell transfected with an expression vector comprising a nucleic acid sequence encoding an isolated *S. pneumoniae* surface associated PPP having a molecular weight of about 20 kDa, where the molecular weight is determined using a 10–20% SDS-PAGE gel, or a fragment thereof; the PPP having the ability to reduce colonization of pneumococcal bacteria, where the sequence is operatively associated with an expression control sequence; and (2) a pharmaceutically acceptable carrier.

The present invention contemplates a composition comprising (1) a host cell transfected with a vector comprising a nucleic acid sequence encoding an isolated *S. pneumoniae* surface associated PPP having a molecular weight of about 20 kDa, where the molecular weight is determined using a 10–20% SDS-PAGE gel, or a fragment thereof; the PPP having the ability to reduce colonization of pneumococcal bacteria, where the sequence is operatively associated with an expression control sequence; where the PPP has an amino acid sequence as depicted in SEQ ID NO: 5, or a fragment thereof; and a (2) pharmaceutically acceptable carrier.

The present invention also contemplates an immunogenic composition comprising (i) a *S. pneumoniae* surface associated PPP having a molecular weight of about 20 kDa, where the molecular weight is determined using a 10–20% SDS-PAGE gel, or a fragment thereof; (ii) a pharmaceutically acceptable carrier; and (iii) optionally at least one adjuvant.

The present invention also contemplates an immunogenic composition comprising (i) a *S. pneumoniae* surface associated PPP having a molecular weight of about 20 kDa, where the molecular weight is determined using a 10–20% SDS-PAGE gel, or a fragment thereof, the PPP having an isoelectric point of about 4.587; (ii) a pharmaceutically acceptable carrier; and (iii) optionally at least one adjuvant.

The present invention also contemplates an immunogenic composition comprising (i) a *S. pneumoniae* surface associated PPP having a molecular weight of about 20 kDa, where the molecular weight is determined using a 10–20% SDS-PAGE gel, or a fragment thereof, PPP having an isoelectric point of about 4.587 and a charge of about −14.214 at pH 7; (ii) a pharmaceutically acceptable carrier; and (iii) optionally at least one adjuvant.

The present invention also contemplates an immunogenic composition comprising (i) a *S. pneumoniae* surface associated PPP having a molecular weight of about 20 kDa, where the molecular weight is determined using a 10–20% SDS-PAGE gel, or a fragment thereof, which PPP has an amino acid sequence as depicted in SEQ ID NO: 5, or an immunogenic fragment thereof; (ii) a pharmaceutically acceptable carrier; and (iii) optionally at least one adjuvant.

The present invention also contemplates an immunogenic composition comprising (i) a *S. pneumoniae* surface associated PPP having a molecular weight of about 20 kDa, where the molecular weight is determined using a 10–20% SDS-PAGE gel, or a fragment thereof, the PPP encoded by a nucleic acid sequence having a sequence as depicted in SEQ ID NO: 4, or an immunogenic fragment thereof; (ii) a pharmaceutically acceptable carrier; and (iii) optionally at least one adjuvant.

The present invention also contemplates an immunogenic composition comprising (i) a *S. pneumoniae* surface associated PPP having a molecular weight of about 20 kDa, where the molecular weight is determined using a 10–20% SDS-PAGE gel, or a fragment thereof; (ii) a pharmaceutically acceptable carrier; and (iii) optionally at least one adjuvant; where the composition elicits protective immunity from a disease caused by *Streptococcus pneumoniae*.

The present invention also contemplates an immunogenic composition comprising (i) a *S. pneumoniae* surface associated PPP having a molecular weight of about 20 kDa, where the molecular weight is determined using a 10–20% SDS-PAGE gel, or a fragment thereof; (ii) a pharmaceutically acceptable carrier; and (iii) optionally at least one adjuvant; where the composition elicits protective immunity from a disease caused by *Streptococcus pneumoniae*; where the disease is selected from the group consisting of otitis media, rhinosinusitis, bacteremia, meningitis, pneumonia, and lower respiratory tract infection.

The present invention also contemplates an immunogenic composition comprising (i) a *S. pneumoniae* surface associated PPP having a molecular weight of about 20 kDa, where the molecular weight is determined using a 10–20% SDS-PAGE gel, or a fragment thereof; (ii) a pharmaceutically acceptable carrier; and (iii) optionally at least one adjuvant; where the composition elicits protective immunity from a disease caused by *Streptococcus pneumoniae*; where the PPP comprises an amino acid sequence as depicted in SEQ ID NO: 5, or an immunogenic fragment thereof.

The present invention also contemplates an immunogenic composition comprising (i) a *S. pneumoniae* surface associated PPP having a molecular weight of about 20 kDa, where the molecular weight is determined using a 10–20% SDS-PAGE gel, or a fragment thereof where the PPP is encoded by a nucleic acid sequence as depicted in SEQ ID NO: 4, or an immunogenic fragment thereof; (ii) a pharmaceutically acceptable carrier; and (iii) optionally at least one adjuvant; where the composition elicits protective immunity from a disease caused by Streptococcus pneumoniae.

The present invention contemplates an immunogenic composition comprising (i) at least one expression vector encoding a PPP having a molecular weight of about 20 kDa, where the molecular weight is determined using a 10–20% SDS-PAGE gel; (ii) a pharmaceutically acceptable carrier; and (iii) optionally at least one adjuvant.

The present invention contemplates an immunogenic composition comprising (i) at least one expression vector encoding a PPP having a molecular weight of about 20 kDa, where the molecular weight is determined using a 10–20% SDS-PAGE gel; (ii) a pharmaceutically acceptable carrier; and (iii) optionally at least one adjuvant; where the pneumococcal bacteria is *Streptococcus pneumoniae*.

The present invention contemplates an immunogenic composition comprising (i) at least one expression vector encoding a PPP having a molecular weight of about 20 kDa, where the molecular weight is determined using a 10–20% SDS-PAGE gel; (ii) a pharmaceutically acceptable carrier; and (iii) optionally at least one adjuvant; where the composition elicits protective immunity from a disease caused by *Streptococcus pneumoniae*.

The present invention contemplates an immunogenic composition comprising (i) at least one expression vector encoding a PPP having a molecular weight of about 20 kDa, where the molecular weight is determined using a 10–20% SDS-PAGE gel; (ii) a pharmaceutically acceptable carrier; and (iii) optionally at least one adjuvant; where the composition elicits protective immunity from a disease caused by *Streptococcus pneumoniae*; where the disease is selected from the group consisting of otitis media, rhinosinusitis, bacterenia, meningitis, pneumonia, and lower respiratory tract infection.

The present invention contemplates an immunogenic composition comprising (i) at least one expression vector encoding a PPP having a molecular weight of about 20 kDa, where the molecular weight is determined using a 10–20% SDS-PAGE gel, where the PPP has an isoelectric point of about 4.587; (ii) a pharmaceutically acceptable carrier; and (iii) optionally at least one adjuvant.

The present invention contemplates an immunogenic composition comprising (i) at least one expression vector encoding a PPP having a molecular weight of about 20 kDa, where the molecular weight is determined using a 10–20% SDS-PAGE gel, where the PPP has an isoelectric point of about 4.587 and has a charge of about 14.214 at pH7; (ii) a pharmaceutically acceptable carrier; and (iii) optionally at least one adjuvant.

The present invention contemplates an immunogenic composition comprising (i) at least one expression vector encoding a PPP having a molecular weight of about 20 kDa, where the molecular weight is determined using a 10–20% SDS-PAGE gel where expression vector comprises a nucleic acid sequence encoding an amino acid sequence as depicted in SEQ ID NO: 5, or an immunogenic fragment thereof; (ii) a pharmaceutically acceptable carrier; and (iii) optionally at least one adjuvant.

The present invention contemplates an immunogenic composition comprising (i) at least one expression vector encoding a PPP having a molecular weight of about 20 kDa, where the molecular weight is determined using a 10–20% SDS-PAGE gel where the expression vector comprises a nucleic acid sequence encoding an amino acid sequence as depicted in SEQ ID NO: 5, or an immunogenic fragment thereof; (ii) a pharmaceutically acceptable carrier; and (iii) optionally at least one adjuvant.

The present invention contemplates an immunogenic composition comprising (i) at least one expression vector encoding a PPP having a molecular weight of about 20 kDa, where the molecular weight is determined using a 10–20% SDS-PAGE gel where the expression vector comprises a nucleic acid sequence depicted in SEQ ID NO:4, or an immunogenic fragment thereof; (ii) a pharmaceutically acceptable carrier; and (iii) optionally at least one adjuvant.

The present invention contemplates a method of inducing an immune response in a mammal, the method comprising administering to the mammal an amount of a composition effective to induce an immune response in the mammal; where the composition comprises (i) a *S. pneumoniae* surface associated PPP having a molecular weight of about 20 kilo Daltons (kDa), wherein said molecular weight is determined using a 10–20% SDS-PAGE gel, or a fragment thereof; (ii) a pharmaceutically acceptable carrier; and (iii) optionally at least one adjuvant.

The present invention contemplates a method of inducing an immune response in a mammal, the method comprising administering to the mammal an amount of an immunogenic composition effective to induce an immune response in the mammal; where the composition comprises (i) a *S. pneumoniae* surface associated PPP having a molecular weight of about 20 kDa, where the molecular weight is determined using a 10–20% SDS-PAGE gel, or a fragment thereof, which PPP has an amino acid sequence as depicted in SEQ ID NO: 5, or an immunogenic fragment thereof; (ii) a pharmaceutically acceptable carrier; and (iii) optionally at least one adjuvant.

The present invention contemplates a method of inducing an immune response in a mammal, the method comprising administering to the mammal an amount of an immunogenic composition effective to induce an immune response in the mammal; where the composition comprises (i) at least one expression vector encoding a PPP having a molecular weight of about 20 kDa, wherein said molecular weight is determined using a 10–20% SDS-PAGE gel, where the PPP having an isoelectric point of about 4.582; (ii) a pharmaceutically acceptable carrier; and (iii) optionally at least one adjuvant.

The present invention contemplates a method of inducing an immune response in a mammal, the method comprising administering to the mammal an amount of a composition effective to induce an immune response in the mammal; where the composition comprises (i) at least one expression vector encoding a PPP having a molecular weight of about 20 kDa, wherein said molecular weight is determined using a 10–20% SDS-PAGE gel; (ii) a pharmaceutically acceptable carrier; and (iii) optionally at least one adjuvant; wherein said expression vector comprises a nucleic acid sequence encoding an amino acid sequence as depicted in SEQ ID NO: 5, or an immunogenic fragment thereof.

The present invention contemplates a method of inducing an immune response in a mammal which is infected with pneumococcal bacteria, the method comprising administering to the mammal an amount of a compound effective to inhibit binding of an amino acid sequence as depicted in SEQ ID NO: 5 to induce the immune response in the mammal.

The present invention also contemplates a method for screening for a compound which induces an immune response in a mammal infected with pneumococcal bacteria, the method comprising comparing a first amount of binding of an amino acid sequence as depicted in SEQ ID NO: 5 in the presence of the compound to a second amount of binding of an amino acid sequence as depicted in SEQ ID NO: 5 not in the presence of the compound; whereby a lower first amount of binding than the second amount binding indicates that the compound may induce the immune response in the mammal.

The present invention also contemplates a method for diagnosing pneumococcal bacterial infection, the method comprising comparing the level of PPP as depicted in SEQ ID NO: 5, or fragments thereof, in suspect sample to the level of PPP as depicted in SEQ ID NO: 5, or fragments thereof, in a control sample, whereby a higher level of the Pneumo Protective Protein the suspect sample than the level of the Pneumo Protective Protein in the control sample indicates that the suspect sample comprises pneumococcal bacterial infection.

The present invention further contemplates an antibody which binds to Streptococcus pneumoniae PPP.

The present invention also contemplates an antibody which binds to Streptococcus pneumoniae PPP, which selectively recognizes an amino acid sequence as depicted in SEQ ID NO: 5, or fragments thereof.

The present invention also contemplates a chimeric antibody which binds to Streptococcus pneumoniae PPP.

The present invention also contemplates a humanized antibody which binds to Streptococcus pneumoniae PPP.

The present invention also contemplates an anti-idiotypic antibody which binds to Streptococcus pneumoniae PPP.

The present invention also contemplates an antibody which binds to Streptococcus pneumoniae PPP, where the antibody is conjugated to a pharmaceutically active compound.

The present invention also contemplates a monoclonal antibody which binds to Streptococcus pneumoniae PPP.

The present invention also contemplates a monoclonal antibody which binds to Streptococcus pneumoniae PPP, where the antibody is humanized.

The present invention also contemplates a monoclonal antibody which binds to Streptococcus pneumoniae PPP, where the antibody is anti-idiotypic.

The present invention also contemplates a monoclonal antibody which binds to Streptococcus pneumoniae PPP, where the antibody is conjugated to a pharmaceutically active compound.

The present invention contemplates a method for inducing an immune response in a mammal, the method comprising administering to the mammal an amount of an anti-idiotypic antibody which binds to Streptococcus pneumoniae PPP which is effective to induce an immune response in the mammal.

The present invention contemplates a method for inducing an immune response in a mammal, the method comprising administering to the mammal an amount of a monoclonal antibody which binds to Streptococcus pneumoniae PPP, where the antibody is anti-idiotypic; effective to induce an immune response in the mammal.

The present invention contemplates a method for inducing an immune response in a mammal infected with pneumococcal bacteria, the method comprising administering to the mammal an amount of an antibody which binds to Streptococcus pneumoniae PPP, where the antibody is conjugated to a pharmaceutically active compound; effective to induce an immune response in the mammal.

The present invention also contemplates a method for inducing an immune response in a mammal infected with pneumococcal bacteria, the method comprising administering to the mammal an amount of a monoclonal antibody which binds to Streptococcus pneumoniae PPP, where the antibody is conjugated to a pharmaceutically active compound; effective to induce an immune response in the mammal.

BRIEF DESCRIPTION OF THE DRAWINGS

FIGS. 6A and 6B. Comparison of sequences of PPP1 from serotypes of S. pneumoniae.

DETAILED DESCRIPTION

Figure 1:
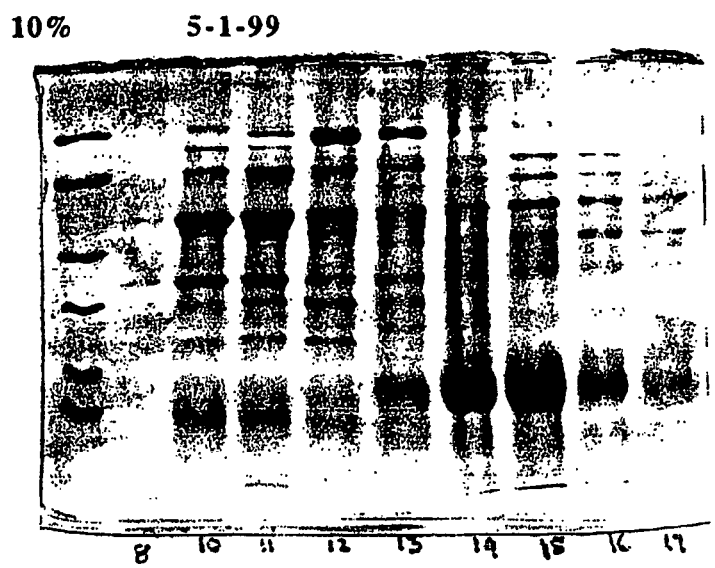
FIG. 1. SDS-PAGE gel of DEAE fractions from PBS washes of S. pneumoniae strain 49136. Lane 1 is unstained standards; lane 2 is fraction #8; lane 3 is fraction #9; lane 4 is fraction #10; lane 5 is fraction #11; lane 6 is fraction #12; lane 7 is fraction #13; lane 8 is fraction #19; lane 9 is fraction #15; and lane 10 is fraction #16. The gel in FIG. 1 shows the distinct small molecular weight band in fractions #14 and #15 (lanes 8 and 9) resolved by the gel.

The proteins and nucleic acids of this invention possess diagnostic, prophylactic and therapeutic utility for diseases caused by Streptococcus pneumoniae infection. They can be used to design screening systems for compounds that interfere or disrupt interaction of proteins associated with S. pneumoniae with iron. The nucleic acids and proteins also can be used in the preparation of compositions against S. pneumoniae infection and/or other pathogens when used to express foreign genes.

In the present invention, a recombinant 20 kDa protein from whole S. pneumoniae that reduces colonization of S. pneumoniae, in an intranasal challenge model, has been identified. The protein described herein has been named Pneumo Protective Protein 1 (PPP1). This protein shows significant homology to a non heme containing ferretin protein from L. innocua, which interestingly, is a member of the Dps family of DNA binding proteins (Pikis, A., et al., J. Infect. Diseases, 1998, 178:700). The ability of this protein to reduce colonization was thus unexpected, due to its predicted location in the cytoplasm.

Chemical studies indicate that the isolated S. pneumoniae surface associated PPP has a molecular weight of about 20 kDa, where the molecular weight is determined using a 10–20% SDS-PAGE gel. The recombinant PPP is determined to have an isoelectric point of about 4.587. Additionally, the protein has a charge of about −14.214 at pH of about 7.

Streptococcus Pneumoniae

S. pneumoniae is a species of bacteria which is highly infectious in the human body. There have been more than 80 serotypes identified, to date. Several of these serotypes are etiological agents in a variety of disease states including, but not limited to, pneumonia, meningitis, endocarditis, arthritis, sinusitis, otitis, bronchitis, and laryngitis. Pneumococcal infections have been identified as a leading cause of death in persons with immunocompromised systems, such as those infected with HIV.

S. pneumoniae is a species of the Streptococcus genus of the Streptococceaceae family. This family comprises Gram-positive, non-motile, spherical or oval cells that do not form endospores. S. pneumoniae have an inorganic terminal electron acceptor for oxidative-metabolism; however, they will grow in the presence of oxygen. This allows S. pneumoniae to grow in a variety of environments and thus it is well adapted to grow in various human tissues. The bacteria is difficult to target with penicillin, since many strains produce a polysaccharide capsule.

The first step towards pneumococcal infection is colonization of the nasopharynx. Disruption of binding of the pneumococci to human nasopharyngeal/otic cells should result in reduction of colonization and a lower disease potential. Thus, isolation of the structures responsible for pneumococcal binding to human cells could lead to vaccine candidates. Pneumococci have evolved numerous mechanisms for binding to human nasopharyngeal cells, including the PspA, PsaA, and CbpA proteins. Additionally, pneumococci may specifically bind to human nasopharyngeal mucin as a first step in colonization. Thus, identification of the pneumococcal structure(s) responsible for this interaction may identify potential vaccine targets.

Molecular Biology

Embodiments of this invention relate to isolated polynucleotide sequences encoding the polypeptides or proteins, as well as variants of such sequences. Preferably, under high stringency conditions, these variant sequences hybridize to polynucleotides encoding one or more pneumo protective proteins. More preferably, under high stringency conditions, these variant sequences hybridize to polynucleotides encoding one or more pneumo protective protein sequences, such as the polynucleotide sequence of SEQ ID NO: 4. For the purposes of defining high stringency southern hybridization conditions, reference can conveniently be made to Sambrook et al. (1989) at pp. 387–389 which is herein incorporated by reference, where the washing step is considered high stringency.

This invention also relates to conservative variants wherein the polynucleotide sequence differs from a reference sequence through a change to the third nucleotide of a nucleotide triplet. Preferably these conservative variants function as biological equivalents to the PPP1 reference polynucleotide sequence. In a preferred embodiment, variants that function as biological equivalents are those that bind to iron.

The present invention further comprises DNA sequences which, by virtue of the redundancy of the genetic code, are biologically equivalent to the sequences which encode for the PPP1, that is, these other DNA sequences are characterized by nucleotide sequences which differ from those set forth herein, but which encode a protein having the same amino acid sequence as that encoded by the DNA sequence in SEQ ID NO: 4.

This invention also comprises DNA sequences which encode amino acid sequences which differ from those of the S. pneumonia PPP1, but which are biologically equivalent to those described for this protein (SEQ ID NO: 5). Such amino acid sequences may be said to be biologically equivalent to such PPP1 if their sequences differ only by minor deletions from, insertions into or substitutions to the PPP1 sequence, such that the tertiary configurations of the sequences are essentially unchanged from those of the wild-type protein.

For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, as well as changes based on similarities of residues in their hydropathic index, can also be expected to produce a biologically equivalent product. Nucleotide changes which result in alteration of the N-terminal or C-terminal portions of the protein molecule would also not be expected to alter the activity of the protein.

One can use the hydropathic index of amino acids in conferring interactive biological function on a polypeptide, as discussed by Kyte and Doolittle (1982), wherein it was determined that certain amino acids may be substituted for other amino acids having similar hydropathic indices and still retain a similar biological activity. Alternatively, substitution of like amino acids may be made on the basis of hydrophilicity, particularly where the biological function desired in the polypeptide to be generated is intended for use in immunological embodiments. See, for example, U.S. Pat. No. 4,554,101 (which is hereby incorporated herein by reference), which states that the greatest local average hydrophilicity of a "protein," as governed by the hydrophilicity of its adjacent amino acids, correlates with its immunogenicity. Accordingly, it is noted that substitutions can be made based on the hydrophilicity assigned to each amino acid. In using either the hydrophilicity index or hydropathic index, which assigns values to each amino acid, it is preferred to introduce substitutions of amino acids where these values are±2, with±1 being particularly preferred, and those within±0.5 being the most preferred substitutions.

Furthermore, changes in known variable regions are biologically equivalent where the tertiary configurations of the conserved regions are essentially unchanged from those of PPP1. An alternative definition of a biologically equivalent sequence is one that is still capable of generating a cross-reactive immune response. In particular, the proteins may be modified by lengthening or shortening the corresponding insertion from the gonococcal pilin, as long as the modified protein is still capable of generating a desired immune response.

Each of the proposed modifications is well within the routine skill in the art, as is determination of retention of structural and biological activity of the encoded products. Therefore, where the terms "pneumo protective protein", or "PPP1", or "PPP" are used in either the specification or the claims, it will be understood to encompass all such modifications and variations which result in the production of a biologically equivalent protein.

Preferable characteristics of PPP1 described herein, encoded by the nucleotide sequences of this invention, include one or more of the following: (a) being a membrane protein or being a protein directly associated with a membrane; (b) capable of being separated as a protein using an SDS acrylamide gel; and (c) retaining its biological function of interacting with iron.

Variants and fragments may be attenuated, i.e. having reduced on no iron-binding activity when compared to wild-type PPP1 of the present invention. Preferably, the fragments and variant amino acid sequences and variant nucleotide sequences expressing PPP1 are biological equivalents, i.e. they retain substantially the same function of the wild-type PPP1. Such variant amino acid sequences are encoded by polynucleotides sequences of this invention. Such variant amino acid sequences may have about 70% to about 80%, and preferably about 90%, overall similarity to the amino acid sequence of PPP1. In a preferred embodiment, these sequences are shown in FIG. 6 and SEQ ID NOs10–19. The variant nucleotide sequences may have either about 70% to about 80%, and preferably about 90%, overall similarity to the nucleotide sequences which, when transcribed, encode the amino acid sequence of PPP1 or a variant amino acid sequence of PPP1. The attenuated proteins of the present invention comprise at least one epitopic region of the wild-type protein. In alternative embodiments, the epitopic region of the protein comprises at least 20 contiguous nucleotides or 8 contiguous amino acids.

The invention further relates to the overall consensus sequence of PPP1. Deduced amino acid sequences of PPP1 from different serotypes of S. pneumoniae may be compared to determine the conserved sequences. In a one embodiment, 10 different serotypes are compared. The conserved sequence may have many uses such as, but not limited to, determining the minimal requirements needed for protein binding, activity, and/or function. In a preferred embodiment, the consensus sequence of PPP1 is depicted in FIG. 6 and SEQ ID NO:20.

The "isolated" sequences of the present invention are non-naturally occurring sequences. For example, these sequences can be isolated from their normal state within the genome of the bacteria; or the sequences may be synthetic, i.e. generated via recombinant techniques, such as well-known recombinant expression systems, or generated by a machine.

The invention also provides a recombinant DNA cloning vehicle capable of expressing a PPP1 comprising an expression control sequence having promoter and initiator sequences and a nucleic acid sequence of the present invention located 3' to the promoter and initiator sequences. Cloning vehicles can be any plasmid or expression vector known in the art, including viral vectors (see below). In a further aspect, there is provided a host cell containing a recombinant DNA cloning vehicle and/or a recombinant PPP1 of the present invention. Suitable expression control sequences, host cells and expression vectors are well known in the art, and are described by way of example, in Sambrook et al. (1989).

Suitable host cells may be selected based on factors which can influence the yield of recombinantly expressed proteins. These factors include, but are not limited to, growth and induction conditions, mRNA stability, codon usage, translational efficiency and the presence of transcriptional terminators to minimize promoter read through. Upon selection of suitable host cells, the cell may be transfected with expression vectors comprising nucleic acid sequences of the present invention. The cells may be transfected using any methods known in the art (see below).

Once host cells have been transfected with expression vectors of the present invention, cells are cultured under conditions such that polypeptides are expressed. The polypeptide is then isolated substantially free of contaminating host cell components by techniques that are well known to those skilled in the art.

Depending on the application of the desired recombinant proteins, a heterologous nucleotide sequence may encode a co-factor, cytokine (such as an interleukin), a T-helper epitope, a restriction marker, adjuvant, or a protein of a different microbial pathogen (e.g. virus, bacterium, fungus or parasite), especially proteins capable of eliciting a protective immune response. It may be desirable to select a heterologous sequence that encodes an immunogenic portion of a co-factor, cytokine (such as an interleukin), a T-helper epitope, a restriction marker, adjuvant, or a protein of a different microbial pathogen (e.g. virus, bacterium or fungus). Other types of non-PPP1 moieties include, but are not limited to, those from cancer cells or tumor cells, allergens, amyloid peptide, protein or other macromolecular components.

For example, in certain embodiments, the heterologous genes encode cytokines, such as interleukin-12, which are selected to improve the prophylatic or therapeutic characteristics of the recombinant proteins.

Examples of such cancer cells or tumor cells include, but are not limited to, prostate specific antigen, carcino-embryonic antigen, MUC-1, Her2, CA-125 and MAGE-3.

Examples of such allergens include, but are not limited to, those described in U.S. Pat. No. 5,830,877 and published International Patent Application Number WO 99/51259, which are hereby incorporated by reference, and include pollen, insect venoms, animal dander, fungal spores and drugs (such as penicillin). Such components interfere with the production of IgE antibodies, a known cause of allergic reactions.

Amyloid peptide protein (APP) has been implicated in diseases referred to variously as Alzheimer's disease, amyloidosis or amyloidogenic disease. The β-amyloid peptide (also referred to as Aβ peptide) is a 42 amino acid fragment of APP, which is generated by processing of APP by the β and γ secretase enzymes, and has the following sequence:

Asp Ala Glu Phe Arg His Asp Ser Gly Tyr Glu Val His His Gln Lys Leu Val Phe Phe Ala Glu Asp Val Gly Ser Asn Lys Gly Ala Ile Ile Gly Leu Met Val Gly Gly Val Val Ile Ala (SEQ ID NO: 6).

In some patients, the amyloid deposit takes the form of an aggregated Aβ peptide. Surprisingly, it has now been found that administration of isolated Aβ peptide induces an immune response against the Aβ peptide component of an amyloid deposit in a vertebrate host (See Published International Patent Application WO 99/27944). Such Aβ peptides have also been linked to unrelated moieties. Thus, the heterologous nucleotides sequences of this invention include the expression of this Aβ peptide, as well as fragments of Aβ peptide and antibodies to Aβ peptide or fragments thereof. One such fragment of Aβ peptide is the 28 amino acid peptide having the following sequence (as disclosed in U.S. Pat. No. 4,666,829):

Asp Ala Glu Phe Arg His Asp Ser Gly Tyr Glu Val His His Gln Lys Leu Val Phe Phe Ala Glu Asp Val Gly Ser Asn Lys (SEQ ID NO: 7).

The heterologous nucleotide sequence can be selected to make use of the normal route of infection of pneumococcal bacteria, which enters the body through the respiratory tract and can infect a variety of tissues and cells, for example, the meninges, blood, and lung. The heterologous gene may also be used to provide agents which are used for gene therapy or for the targeting of specific cells. As an alternative to merely taking advantage of the normal cells exposed during the normal route of pneumococcal infection, the heterologous gene, or fragment, may encode another protein or amino acid sequence from a different pathogen which, when employed as part of the recombinant protein, directs the recombinant protein to cells or tissue which are not in the normal route of infection. In this manner, the protein becomes a targeting tool for the delivery of a wider variety of foreign proteins.

Molecular weight of proteins may be determined by using any method known in the art. A non-limiting list of methods includes, denaturing SDS-PAGE gel, size exclusion chromatography, and iso-electric focusing. Conditions appropriate for each method (e.g. time of separation, voltage, current, and buffers) can be determined as needed using defined methods in the art. In a preferred embodiment, denaturing SDS-PAGE is used to determine the molecular weight of the proteins. Additionally, the conditions used to determine the molecular weight are preferably, 1 hour separation time at 20 milli Amps and constant current.

Detection of the proteins can be determined using various methods in the art. These methods include, but are not limited to, Western blotting, coomassie blue staining, silver staining, autoradiography, fluorescent and phosphorescent probing. In a preferred embodiment of this invention, the proteins were detected by Western blotting.

The terms "pneumo protective protein", "PPP1", and "PPP" in describing embodiments of the invention, infra, includes embodiments that employ fragments, variants and attenuated forms thereof as a replacement for wild-type PPP1 or as addition thereto, unless specified otherwise.

Viral and Non-Viral Vectors

Preferred vectors, particularly for cellular assays in vitro and in vivo, are viral vectors, such as lentiviruses, retroviruses, herpes viruses, adenoviruses, adeno-associated viruses, vaccinia virus, baculovirus, alphaviruses and other recombinant viruses with desirable cellular tropism. Thus, a gene encoding a functional or mutant protein or polypeptide domain fragment thereof can be introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both. Targeted gene delivery is described in PCT Publication No. WO 95/28494.

Viral vectors commonly used for in vivo or ex vivo targeting and therapy procedures are DNA-based vectors and retroviral vectors. Methods for constructing and using viral vectors are known in the art (e.g., Miller and Rosman, BioTechniques, 1992, 7:980–990). Preferably, the viral vectors are replication-defective, that is, they are unable to replicate autonomously in the target cell. Preferably, the replication defective virus is a minimal virus, i.e., it retains only the sequences of its genome which are necessary for encapsulating the genome to produce viral particles.

Examples of alphaviruses include, but are not limited to, Eastern Equine Encephalitis virus (EEE), Venezuelan Equine Encephalitis virus (VEE), Everglades virus, Mucambo virus, Pixuna virus, Western Equine Encephalitis virus (WEE), Sindbis virus, Semliki Forest virus, Middelburg virus, Chikungunya virus, O'nyong-nyong virus, Ross River virus, Barmah Forest virus, Getah virus, Sagiyama virus, Bebaru virus, Mayaro virus, Una virus, Aura virus, Whataroa virus, Babanki virus, Kyzylagach virus, Highlands J virus, Fort Morgan virus, Ndumu virus, and Buggy Creek virus (U.S. Pat. No. 6,156,558).

DNA viral vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Molec. Cell. Neurosci., 1991, 2:320–330), defective herpes virus vector lacking a glyco-protein L gene, or other defective herpes virus vectors (PCT Publication Nos. WO 94/21807 and WO 92/05263); an attenuated adenovirus vector, such as the vector described by Stratford-Perricaudet et al. (J. Clin. Invest., 1992, 90:626–630; see also La Salle et al., Science, 1993, 259: 988–990); and a defective adeno-associated virus vector (Samulski et al., J. Virol., 1987, 61:3096–3101; Samulski et al., J. Virol., 1989, 63:3822–3828; Lebkowski et al., Mol. Cell. Biol., 1988, 8:3988–3996).

Various companies produce viral vectors commercially, including, but not limited to, Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

Adenovirus vectors. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to using type 2 or type 5 human adenoviruses (Ad 2 or Ad 5) or adenoviruses of animal origin (see PCT Publication No. WO 94/26914). Those adenoviruses of animal origin which can be used within the scope of the present invention include adenoviruses of canine, bovine, murine (example: Mav1, Beard et al., Virology, 1990, 75–81), ovine, porcine, avian, and simian (example: SAV) origin. Preferably, the adenovirus of animal origin is a canine adenovirus, more preferably a CAV2 adenovirus (e.g., Manhattan or A26/61 strain, ATCC VR-800, for example). Various replication defective adenovirus and minimum adenovirus vectors have been described (PCT Publication Nos. WO 94/26914, WO 95/02697, WO 94/28938, WO 94/28152, WO 94/12649, WO 95/02697, WO 96/22378). The replication defective recombinant adenoviruses according to the invention can be prepared by any technique known to the person skilled in the art (Levrero et al., Gene, 1991, 101:195; European Publication No. EP 185 573; Graham, EMBO J., 1984, 3:2917; Graham et al., J. Gen. Virol., 1977, 36:59). Recombinant adenoviruses are recovered and purified using standard molecular biological techniques, which are well known to one of ordinary skill in the art.

Adeno-associated viruses. The adeno-associated viruses (AAV) are DNA viruses of relatively small size that can integrate, in a stable and site-specific manner, into the genome of the cells which they infect. They are able to infect a wide spectrum of cells without inducing any effects on cellular growth, morphology or differentiation, and they do not appear to be involved in human pathologies. The AAV genome has been cloned, sequenced and characterized. The use of vectors derived from the AAVs for transferring genes in vitro and in vivo has been described (see, PCT Publication Nos. WO 91/18088 and WO 93/09239; U.S. Pat. Nos.

4,797,368 and 5,139,941; European Publication No. EP 488 528). The replication defective recombinant AAVs according to the invention can be prepared by cotransfecting a plasmid containing the nucleic acid sequence of interest flanked by two AAV inverted terminal repeat (ITR) regions, and a plasmid carrying the AAV encapsidation genes (rep and cap genes), into a cell line which is infected with a human helper virus (for example an adenovirus). The AAV recombinants which are produced are then purified by standard techniques.

Retrovirus vectors. In another embodiment the gene can be introduced in a retroviral vector, e.g., as described in U.S. Pat. No. 5,399,346; Mann et al, Cell, 1983, 33:153; U.S. Pat. Nos. 4,650,764 and 4,980,289; Markowitz et al., J. Virol., 1988, 62:1120; U.S. Pat. No. 5,124,263; European Publication Nos. EP 453 242 and EP178 220; Bernstein et al., Genet. Eng.,1985,7:235; McCormick, BioTechnology, 1985, 3:689; PCT Publication No. WO 95/07358; and Kuo et at., Blood, 1993, 82:845. The retroviruses are integrating viruses that infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Suitable packaging cell lines have been described in the prior art, in particular the cell line PA317 (U.S. Pat. No. 4,861,719); the PsiCRIP cell line (PCT Publication No. WO 90/02806) and the GP+envAm–12 cell line (PCT Publication No. WO 89/07150). In addition, the recombinant retroviral vectors can contain modifications within the LTRs for suppressing transcriptional activity as well as extensive encapsidation sequences which may include a part of the gag gene (Bender et al., J. Virol., 1987, 61:1639). Recombinant retroviral vectors are purified by standard techniques known to those having ordinary skill in the art.

Retroviral vectors can be constructed to function as infectious particles or to undergo a single round of transfection. In the former case, the virus is modified to retain all of its genes except for those responsible for oncogenic transformation properties, and to express the heterologous gene. Non-infectious viral vectors are manipulated to destroy the viral packaging signal, but retain the structural genes required to package the co-introduced virus engineered to contain the heterologous gene and the packaging signals. Thus, the viral particles that are produced are not capable of producing additional virus.

Retrovirus vectors can also be introduced by DNA viruses, which permits one cycle of retroviral replication and amplifies tranfection efficiency (see PCT Publication Nos. WO 95/22617, WO 95/26411, WO 96/39036 and WO 97/19182).

Lentivirus vectors. In another embodiment, lentiviral vectors can be used as agents for the direct delivery and sustained expression of a transgene in several tissue types, including brain, retina, muscle, liver and blood. The vectors can efficiently transduce dividing and nondividing cells in these tissues, and maintain long-term expression of the gene of interest. For a review, see, Naldini, Curr. Opin. Biotechnol., 1998, 9:457–63; see also Zufferey, et al., J. Virol., 1998, 72:9873–80). Lentiviral packaging cell lines are available and known generally in the art. They facilitate the production of high-titer lentivirus vectors for gene therapy. An example is a tetracycline-inducible VSV-G pseudotyped lentivirus packaging cell line that can generate virusparticles at titers greater than 106 IU/ml for at least 3 to 4 days (Kafri, et al., J. Virol., 1999, 73: 576–584). The vector produced by the inducible cell line can be concentrated as needed for efficiently transducing non-dividing cells in vitro and in vivo.

Non-viral vectors. In another embodiment, the vector can be introduced in vivo by lipofection, as naked DNA, or with other transfection facilitating agents (peptides, polymers, etc.). Synthetic cationic lipids can be used to prepare liposomes for in vivo transfection of a gene encoding a marker (Felgner, et. al., Proc. Natl. Acad. Sci. U.S.A., 1987, 84:7413–7417; Felgner and Ringold, Science, 1989, 337: 387–388; see Mackey, et al., Proc. Natl. Acad. Sci. U.S.A., 1988, 85:8027–8031; Ulmer et al., Science, 1993, 259: 1745–1748). Useful lipid compounds and compositions for transfer of nucleic acids are described in PCT Patent Publication Nos. WO 95/18863 and WO 96/17823, and in U.S. Pat. No. 5,459,127. Lipids may be chemically coupled to other molecules for the purpose of targeting (see Mackey, et. al., supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., PCT Patent Publication No. WO 95/21931), peptides derived from DNA binding proteins (e.g., PCT Patent Publication No. WO 96/25508), or a cationic polymer (e.g., PCT Patent Publication No. WO 95/21931).

It is also possible to introduce the vector in vivo as a naked DNA plasmid. Naked DNA vectors for gene therapy can be introduced into the desired host cells by methods known in the art, e.g., electroporation, microinjection, cell fusion, DEAE dextran, calcium phosphate precipitation, use of a gene gun, or use of a DNA vector transporter (e.g., Wu et al., J. Biol. Chem., 1992, 267:963–967; Wu and Wu, J. Biol. Chem., 1988, 263:14621–14624; Canadian Patent Application No. 2,012,311; Williams et al., Proc. Natl. Acad. Sci. USA, 1991, 88:2726–2730). Receptor-mediated DNA delivery approaches can also be used (Curiel et al., Hum. Gene Ther., 1992, 3:147–154; Wu and Wu, J. Biol. Chem., 1987, 262:4429–4432). U.S. Pat. Nos. 5,580,859 and 5,589, 466 disclose delivery of exogenous DNA sequences, free of transfection facilitating agents, in a mammal. Recently, a relatively low voltage, high efficiency in vivo DNA transfer technique, termed electrotransfer, has been described (Mir et al., C. P. Acad. Sci., 1988, 321:893; PCT Publication Nos. WO 99/01157; WO 99/01158; WO 99/01175).

Assay System

Any cell assay system that allows for assessing functional activities of immunogenic compositions and compounds that modulate binding of PPP1 to iron is contemplated by the present invention. In a specific embodiment, the assay can be used to identify compounds that interact with PPP1 to decrease binding of PPP1, described herein, to iron. This can be evaluated by assessing the effects of a test compound on the interaction the protein described herein. A cell assay system that assesses the ability of the compound to elicit opsonophagocytic antibodies against *S. pneumoniae* may also be utilized (Gray, B. M. 1990. Conjugate Vaccines Supplement p694–697).

Any convenient method that permits detection of the binding of iron with PPP are contemplated by the present invention. In a preferred embodiment of the invention, protein components of *S. pneumoniae* can be separated on a polyacrylamide gel and transferred to a solid support. The support then may be probed with a labeled interacting component (e.g. iron). The component may be labeled with any label known in the art including, but not limited to, radioactivity, enzyme-based, dye molecules, or a flourescent or phosphorescent tag. In a preferred embodiment, the label is radioactive. The label may be detected by any means known in the art. For example, autoradiography, scintillation counter, or ultra-violet light. In a preferred embodiment, the radiolabel is detected by autoradiography. Assays that amplify the signals from the probe are also known, such as, for example, those that utilize biotin and avidin, and enzyme-labeled immunoassays, such as ELISA assays.

In Vitro Screening Methods

Candidate agents are added to assay systems, prepared by known methods in the art, and the level of binding between iron and PPP1 is measured. Various in vitro systems can be used to analyze the effects of a compound on iron binding. Preferably, each experiment is performed more than once, such as, for example, in triplicate at multiple different dilutions of compound.

The screening system of the invention permits detection of binding inhibitors. An inhibitor screen involves detecting interaction of iron and PPP1 when contacted with a compound that regulates interaction of these proteins. If a decrease in the binding of iron to PPP1 is detected, then the compound is a candidate inhibitor. If no decrease is observed, the compound does not alter the binding of iron to the protein of the present invention.

Immunogenic Compositions

In further embodiments of this invention PPP1 are employed in immunogenic compositions comprising (i) at least one PPP1; (ii) at least one pharmaceutically acceptable buffer, diluent, or carrier; and (iii) optionally at least one adjuvant. In a preferred embodiment, the immunogenic composition is used as a vaccine. The PPP1 may be recombinantly produced or isolated from a bacterial preparation, according to methods known in the art. Preferably, these compositions have therapeutic and prophylactic applications as immunogenic compositions in preventing, protecting and/or ameliorating pneumococcal infection. In such applications, an immunologically effective amount of at least one PPP1 is employed in such amount to cause a reduction, preferably a substantial reduction, in the course a normal pneumoccocal infection. The proteins may be attenuated. The term "attenuated" refers to a protein that maintains its immunogenic activity, while one or more other functional characteristics are decreased or deleted. For example, the attenuated form of this protein may exhibit diminished binding properties, such as its ability to bind iron. Alternatively, the attenuated form may decrease the ability of *S. pneumoniae* to bind iron.

As used herein, the term "effective amount" refers to amount of the immunogen component (i.e. PPP1) described herein to stimulate an immune response, i.e., to cause the production of antibodies and/or a cell-mediated response when introduced into a subject. In a preferred embodiment, the effective amount will decrease the colonization of *S. pneumoniae*. The term "immunogen component" refers to the ability of this component to stimulate secretory antibody and/or cell-mediated response production in local regions, e.g. nasopharynx, when administered systemically as an immunogenic composition according to the present invention.

As used herein the term "adjuvant" refers to an agent, compound or the like, which potentiates or stimulates the immune response in a subject when administered in combination with the immunogenic composition. Thus, the immune response, elicited by the immunogenic composition combination, as measured by any convention method known in the art, will generally be greater than that provoked by the immunogenic composition alone.

The compositions of the invention can include an adjuvant, including, but not limited to aluminum hydroxide; aluminum phosphate; Stimulon™ QS-21 (Aquila Biopharmaceuticals, Inc., Framingham, Mass.); MPL™ (3-O-deacylated monophosphoryl lipid A; Corixa, Seattle, Wash.); RC529 (Corixa) and aminoalkyl glucosamine phosphate compounds as described in PCT Published Application WO 98/50399 (RIBI Immunochem Research); IL-12 (Genetics Institute, Cambridge, Mass.); N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to a MTP-PE); granulocyte-macrophage colony stimulating factor (GM-CSF) and cholera toxin. Others which may be used are non-toxic derivatives of cholera toxin, including its B subunit (for example, wherein glutamic acid at amino acid position 29 is replaced by another amino acid, preferably, a histidine in accordance with Published International Patent Application WO 00/18434), and/or conjugates or genetically engineered fusions of non-PPP polypeptides with cholera toxin or its B subunit, procholeragenoid, fungal polysaccharides. The adjuvant may be used in its natural form or one can use a synthetic or semi-synthetic version of an adjuvant. Any formulation of the adjuvant may be used depending on the desired response and admininstration method. Various forms of the adjuvant may be used, e.g., a liquid, powder or emulsion.

The immunogenic composition may be administered as a single bolus dose or as a "series" of administrations over a defined period of time (e.g., one year). When given in later year, such series of administrations is referred to as "booster shots". These administrations increase the antibody levels produced by the previous administration. The immunogenic compound may be administered until sufficient antibody levels have been identified in the subject, so as to induce an immune response upon challenge from the immunogen.

The formulation of such immunogenic compositions is well known to persons skilled in this field. Immunogenic compositions of the invention may comprise additional antigenic components (e.g., polypeptide or fragment thereof or nucleic acid encoding an antigen or fragment thereof) and, preferably, include a pharmaceutically acceptable carrier. Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. The term "pharmaceutically acceptable carrier" refers to a carrier that does not cause an allergic reaction or other untoward effect in patients to whom it is administered. Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the antigen. The use of such media and agents for pharmaceutically active substances is well known in the art. Except insofar as any conventional media or agent is incompatible with the active ingredient, use thereof in immunogenic compositions of the present invention is contemplated.

Compositions

In further embodiments of this invention, PPP1 nucleic acid sequences, amino acid sequences, expression vectors or host cells are employed in compositions comprising (i) at least one PPP1 protein, or nucleic acid encoding an amino acid sequence of a PPP1, or an expression vector or host cell that expresses such nucleic acid arid (ii) at least one of a pharmaceutically acceptable buffer, diluent, or carrier. The PPP1 may be recombinantly produced or isolated from a bacterial preparation, according to methods known in the art. Preferably, these compositions have therapeutic and prophylactic applications. In such applications, a pharmaceutically effective amount of at least one PPP1 is employed in such amount to produce a defined functional activity. As used herein, the term "effective amount" refers to amount of the PPP1 protein described herein, to produce a functional effect.

Administration of such compositons or immunogenic compositions may be by any conventional effective form, such as intranasally, parenterally, orally, or topically applied to mucosal surface such as intranasal, oral, eye, lung, vaginal, or rectal surface, such as by aerosol spray. The preferred means of administration is parenteral or intranasal.

Oral formulations include such normally employed excipients as, for example, pharmaceutical grades of mannitol, lactose, starch, magnesium stearate, sodium saccharine, cellulose, magnesium carbonate, and the like.

The polynucleotides and polypeptides of the present invention may be administered as the sole active immunogen in an immunogenic composition. Alternatively, however, the immunogenic composition may include other active immunogens, including other immunologically active antigens from other pathogenic species. Preferably, the pathogenic species that provide other immunologically active antigens are bacterial pathogens, e.g., involved in bacterial infections. Indeed, preferably therapeutic use of the PPP antigen of the invention will be as a component of a multivalent vaccine that includes other bacterial antigens from S. pneumonia or other pathogenic bacteria. The other immunologically active antigens may be replicating agents or non-replicating agents. Replicating agents include, for example, attenuated forms of measles virus, rubella virus, variscella zoster virus (VZV), Parainfluenza virus (PIV), and Respiratory Syncytial virus (RSV).

One of the important aspects of this invention relates to a method of inducing immune responses in a mammal comprising the step of providing to said mammal an immunogenic composition of this invention. The immunogenic composition is a composition which is immunogenic in the treated animal or human such that the immunologically effective amount of the polypeptide(s) contained in such composition brings about the desired response against pneumococcal infection. Preferred embodiments relate to a method for the treatment, including amelioration, or prevention of pneumococcal infection in a human comprising administering to a human an immunologically effective amount of the immunogenic composition. The dosage amount can vary depending upon specific conditions of the individual. This amount can be determined in routine trials by means known to those skilled in the art.

Certainly, the isolated amino acid sequences for the proteins of the present invention may be used in forming subunit immunogenic compositions. They also may be used as antigens for raising polyclonal or monoclonal antibodies and in immunoassays for the detection of anti-PPP1 protein-reactive antibodies. Immunoassays encompassed by the present invention include, but are not limited to, those described in U.S. Pat. No. 4,367,110. (double monoclonal antibody sandwich assay) and U.S. Pat. No. 4,452,901 (western blot), which U.S. Patents are incorporated herein by reference. Other assays include immunoprecipitation of labeled ligands and immunocytochemistry, both in vitro and in vivo.

Methods of Inducing an Immune Response

According to the present invention, colonization of S. pneumoniae involves PPP1 proteins. The present invention provides for methods that prevent pneumococal infections by administering to a subject a therapeutically effective amount of an immunogenic composition that induces an immune response in the subject. These methods include, but are not limited to, administration of an immunogenic composition comprised of at least one PPP1 protein, variant, fragment or attenuated version thereof, or at least one expression vector encoding the protein variant, fragment or attenuated version thereof.

Methods of Inhibiting Pneumococcal Infection

The present invention further provides for methods to induce an immune response in a subject which is infected with pneumococcal bacteria by administering to a subject a therapeutically effective amount of a composition or compound that blocks functional effects associated with the PPP1 proteins. These methods include, but are not limited to, administration of a composition comprised of at least one PPP1 protein or fragments thereof or at least one expression vector encoding a PPP1 protein or administration of a compound that blocks, substantially all or at least in part, a function of the PPP1 proteins.

Methods of Diagnosis

This invention also provides for a method of diagnosing a pneumococcal infection, or identifying a pneumococcal immunogenic compositon strain that has been administered, comprising the step of determining the presence, in a sample, of an amino acid sequence of SEQ ID NO: 5 or any of 10–19. Any conventional diagnostic method may be used. These diagnostic methods can easily be based on the presence of an amino acid sequence or polypeptide. Preferably, such a diagnostic method matches for a polypeptide having at least 10, and preferably at least 20, amino acids which are common to the amino acid sequences of this invention.

The nucleic acid sequences disclosed herein also can be used for a variety of diagnostic applications. These nucleic acids sequences can be used to prepare relatively short DNA and RNA sequences that have the ability to specifically hybridize to the nucleic acid sequences encoding the PPP1 protein. Nucleic acid probes are selected for the desired length in view of the selected parameters of specificity of the diagnostic assay. The probes can be used in diagnostic assays for detecting the presence of pathogenic organisms, or in identifying a pneumococcal immunogenic composition that has been administered, in a given sample. With current advanced technologies for recombinant expression, nucleic acid sequences can be inserted into an expression construct for the purpose of screening the corresponding oligopeptides and polypeptides for reactivity with existing antibodies or for the ability to generate diagnostic or therapeutic reagents. Suitable expression control sequences and host cell/cloning vehicle combinations are well known in the art, and are described by way of example, in Sambrook et al. (1989).

In preferred embodiments, the nucleic acid sequences employed for hybridization studies or assays include sequences that are complementary to a nucleotide stretch of at least about 10, preferably about 15, and more preferably about 20 nucleotides. A variety of known hybridization techniques and systems can be employed for practice of the hybridization aspects of this invention, including diagnostic assays such as those described in Falkow et al., U.S. Pat. No. 4,358,535. Preferably, the sequences recognize or bind a nucleic acid sequence on the PPP1 protein are consecutive.

In general, it is envisioned that the hybridization probes described herein will be useful both as reagents in solution hybridizations as well as in embodiments employing a solid phase. In embodiments involving a solid phase, the test DNA (or RNA) from suspected clinical samples, such as exudates, body fluids (e.g., middle ear effusion, bronchoalveolar lavage fluid) or even tissues, is absorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe). Following washing of the hybridized surface so as to remove nonspecifically bound probe molecules, specific hybridization is detected, or even quantified, by means of the label.

The nucleic acid sequences which encode the PPP1 protein of the invention, or their variants, may be useful in conjunction with PCR* technology, as set out, e.g., in U.S. Pat. No. 4,603,102. One may utilize various portions of any of the PPP1 protein sequences of this invention as oligonucleotide probes for the PCR* amplification of a defined portion of a PPP1 gene, or nucleotide, which sequence may then be detected by hybridization with a hybridization probe containing a complementary sequence. In this manner, extremely small concentrations of the PPP1 nucleic acid sequence may be detected in a sample utilizing the nucleotide sequences of this invention.

The following examples are included to illustrate certain embodiments of the invention. However, those of skill in the art should, in the light of the present disclosure, appreciate that many changes can be made in the specific embodiments which are disclosed and still obtain a like or similar result without departing from the spirit and scope of the invention.

Antibodies

The present invention describes antibodies that may be used to detect the presence of PPP1 proteins present in samples. Additionally, the antibodies (e.g., anti-idiotypic antibodies) may be used to inhibit immune responses to pneumococcal infections.

According to the invention, PPP1 protein polypeptides produced recombinantly or by chemical synthesis, and fragments or other derivatives, may be used as an immunogen to generate antibodies that recognize the polypeptide or portions thereof. The portion of the polypeptide used as an immunogen may be specifically selected to modulate immunogenicity of the developed antibody. Such antibodies include, but are not limited to, polyclonal, monoclonal, humanized, chimeric, single chain, Fab fragments, and an Fab expression library. An antibody that is specific for human PPP1 protein may recognize a wild-type or mutant form of the PPP1 proteins. In a specific embodiment, the antibody is comprised of at least 8 amino acids, preferably from 8–10 amino acids, and more preferably from 15–30 amino acids. Preferably, the antibody recognizes or binds amino acids on PPP1 are consecutive.

Various procedures known in the art may be used for the production of polyclonal antibodies to polypeptides, derivatives, or analogs. For the production of antibody, various host animals, including but not limited to rabbits, mice, rats, sheep, goats, etc, can be immunized by injection with the polypeptide or a derivative (e.g., fragment or fusion protein). The polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, KLH, dinitrophenol, and potentially useful human adjuvants such as BCG ( bacille Calmette-Guerin) and Corynebacterium parvum.

Monoclonal antibodies directed toward a PPP1 protein, fragment, analog, or derivative thereof, may be prepared by any technique that provides for the production of antibody molecules by continuous cell lines in culture may be used. These include but are not limited to the hybridoma technique originally developed by Kohler and Milstein (Nature 256: 495–497, 1975), as well as the trioma technique, the human B-cell hybridoma technique (Kozbor et al., Immunology Today 4:72, 1983; Cote et al., Proc. Natl. Acad. Sci. U.S.A. 80:2026–2030, 1983), and the EBV-hybridoma technique to produce human monoclonal antibodies (Cole et al., in Monoclonal Antibodies and Cancer Therapy, Alan R. Liss, Inc., pp. 77–96, 1985). "Chimeric antibodies" may be produced (Morrison et al., J. Bacteriol. 159:870, 1984; Neuberger et al., Nature 312:604–608, 1984; Takeda et al., Nature 314:452–454, 1985) by splicing the genes from a non-human antibody molecule specific for a polypeptide together with genes from a human antibody molecule of appropriate biological activity.

In the production and use of antibodies, screening for or testing with the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc.

The foregoing antibodies can be used in methods known in the art relating to the localization and activity of the polypeptide, e.g., for Western blotting, imaging the polypeptide in situ, measuring levels thereof in appropriate physiological samples, etc. using any of the detection techniques mentioned above or known in the art. Such antibodies can also be used in assays for ligand binding, e.g., as described in U.S. Pat. No. 5,679,582. Antibody binding generally occurs most readily under physiological conditions, e.g., pH of between about 7 and 8, and physiological ionic strength. The presence of a carrier protein in the buffer solutions stabilizes the assays. While there is some tolerance of perturbation of optimal conditions, e.g., increasing or decreasing ionic strength, temperature, or pH, or adding detergents or chaotropic salts, such perturbations will decrease binding stability.

In a specific embodiment, antibodies that agonize the activity of the PPP1 protein can be generated. In particular, intracellular single chain Fv antibodies can be used to regulate the PPP1 protein. Such antibodies can be tested using the assays described below for identifying ligands.

In another specific embodiment, the antibodies of the present invention are anti-idiotypic antibodies. These antibodies recognize and or bind to other antibodies present in the system. The anti-idiotypic antibodies may be monoclonal, polyclonal, chimeric, humanized.

In another specific embodiment, antibodies of the present invention are conjugated to a secondary component, such as, for example, a small molecule, polypeptide, or polynucleotide. The conjugation may be produced through a chemical modification of the antibody, which conjugates the antibody to the secondary component. The conjugated antibody will allow for targeting of the secondary component, such as, for example, an antibiotic to the site of interest. The secondary component may be of any size or length. In a specific embodiment, the secondary component is a pharmaceutically active compound.

A further aspect of this invention relates to the use of antibodies, as discussed supra, for targeting a pharmaceutical compound. In this embodiment, antibodies against the PPP1 protein are used to present specific compounds to infected sites. The compounds, preferably an antibiotic agent, when conjugated to the antibodies are referred to as targeted compounds or targeted agents. Methods for generating such target compounds and agents are known in the art. Exemplary publications on target compounds and their preparation are set forth in U.S. Pat. Nos. 5,053,934; 5,773,001; and 6,015,562.

EXAMPLES

Materials and Methods

Bacterial Strains and Plasmids

*S. pneumoniae* strains utilized in this work were *S. pneumoniae* CP1200, a nonencapsulated, highly transformable derivative of R36A, a rough variant of D39, a virulent type 2 strain, (Morrison, D. A. et al., J. Bacteriology, 1983, 156:281) was obtained from Margaret Hostetter at Yale University, C T., and *S. pneumoniae* strain 49136 obtained from the ATCC. *S. pneumoniae* were grown to log phase (approx O.D. of 0.6–0.8 at 600 nm) in Todd Hewitt media (DIFCO Lab., Detroit, Mich.) with 0.5% yeast extract (DIFCO) at 37° C. with aeration or on Tryptic Soy (DIFCO) blood agar plates. *Escherichia coli* strains used in this study were BL21(DE3), BLR(DE3) (Novagen, Madison, Wis.), Top10F'(INVITROGEN, San Diego, Calif.), and were grown in SOB media (15) at 37° C. with aeration containing appropriate antibiotics. Plasmids used in this work were PCR2.1 TOPO (INVITROGEN) and pET28a (Novagen). Where specified, chloramphenicol was used at 20 µg/ml, ampicillin at 100 µg/ml, streptomycin at 100 µg/ml, and kanamycin at 25 µg/ml. Restriction enzymes were purchased from New England Biolabs (Beverly, Mass.) and used according to manufactures directions.

Identification of a Surface Associated Protein in Outer Membrane Fractions of *S. pneumoniae*

Extraction of Surface Associated Components

Bacteria were grown in 4 liters of Todd Hewitt broth, and harvested by centrifugation at 8000×g for 30 minutes. The pellet was suspended in ~175 ml of PBS with the aid of a pipette and immediately centrifuged at 20000×g for 30 mm. The wash was filtered through a 0.45 m filter (NALGENE, Rochester, N.Y.), dialyzed and lyophilized.

Ion-exchange Chromatography of Surface Associated Protein Components

The PBS extract of *S. pneumoniae* was dissolved in Tris-HCl, pH 7.6 (10 mM, 100 ml) and subjected to ion exchange chromatography in a column of DEAE-SEPHAROSE CL-6B. After washing the column with the sample buffer, it was eluted first with 200 mM Tris-HCl, pH 7.6 followed by a linear NaCl gradient to a final NaCl concentration of 0.75 M (in 200 mM Tris-HCl, pH 7.6) over 300 ml. Column fractions were analyzed by SDS-PAGE gel. Fractions containing a substantial amount of a surface associated protein of approximately 18–20 kDa were pooled, desalted by CENTRICON SR3 concentrator and lyophilized.

N-terminal Amino Acid Sequence Analysis by PVDF Blot Excision.

The sample was diluted to 1 mg/mL total protein and combined 1:1 with 2×Tris-SDS-β-ME sample loading buffer (0.25 M Tris-HCl pH6.8, 2% SDS, 10% β-mercaptoethanol, 30% glycerol, 0.01% Bromophenol Blue) (Owl Separation, Portsmouth, N.H.) and heated at 100° C. for 5 minutes. Approximately 10 µg of total protein (20 L of heated solution) of sample was loaded in each of ten lanes on a 12 lane, 10 cm×10 cm×1 mm, 10–20% gradient acrylamide/bis-acrylamide gel (Zaxis, Hudson, Ohio). Molecular weight markers (Novex, San Diego, Calif.) were loaded in the two outermost lanes of each side of the gel. Electrophoresis was carried out on an Owl Separations Mini-Gel rig at a constant amperage of 50 mA for 1 hour in BIO-RAD Tris-Glycine-SDS running buffer. The gel was then rinsed with deionized water and transferred to Millipore Immobilon-P PVDF (polyvinylidene fluoride) using a semi-dry blotting system supplied by Owl Separations at constant amperage of 150 mA for 1 hour. The resulting blot was stained with Amido Black (10% acetic acid, 0.1% amido black in deionized water) and destained in 10% acetic acid. The protein band was then excised from all ten lanes using a methanol cleaned scalpel or mini-Exacto knife and placed in the reaction cartridge of the Applied Biosystems 477A Protein Sequencer (Foster City, Calif.). The N-terminal Sequencer was then run under optimal blot conditions for 12 or more cycles (1 cycle Blank, 1 cycle Standard, and 10 or more cycles for desired residue identification). PTH-amino acid detection was done on the Applied Biosystems 120A PTH Analyzer. The cycles were collected both on an analog chart recorder and digitally via the instrument software. N-terminal amino acid assignment was performed by comparison of the analog and digital data to a standard set of PTH-amino acids and their respective retention times on the analyzer (cysteine residues are destroyed during conversion and are not detected).

Subcloning and Expression of the Recombinant 20 kDa Surface Associated Proteins

N-terminal sequence was compared against the NCBI non redundant database located at www.ncbi.nlm.org using the BLAST algorithim developed by Altschul (Altschul, SF, et al., J. Mol-Biol., 1990, 215:403). This showed that the N-terminal sequence had identity to a open reading frame (ORF) in NCBI database. This ORF had been previously sequenced and was listed as an unidentified ORF (Pikis, A. et al., J. Infect. Dis., 1998, 178:700). Subsequent BLAST analysis of the unknown ORF against the public release of the S. pneumoniae genome (serotype 4), made available by The Institute for Genomic Research (TIGR, www.tigr.org), showed the ORF to be present in the genome, but unidentified as well. DNA analyses of the unknown ORF in the S. pneumoniae genomic sequence and primer designs were performed using the DNASTAR (Madison, Wis.) Lasergene DNA and protein analysis software.

Primers flanking the ORF were designed (SEQ ID NOs: 1 and 2) and subsequently synthesized using the ABI 380A DNA synthesizer. To facilitate subcloning the PCR product into the pET28a expression vector, restriction sites were designed into the PCR primers. An Nco1 site was included in the 5' primer, which allowed both for the ligation into the Nco1 site of the expression vector and also included an ATG start codon. To maintain the correct reading frame, two extra bases were included in the 5' primer, resulting in the addition of a codon for Leucine. A Sal1 site was included in the 3' primer.

A PCR fragment of the expected size was generated from CP1200, ligated into the pCR2.1 vector, and used to transform ONE SHOT Top 10F' cell (INVITROGEN). Ampicillin resistant transformants were screened by restriction digestion of plasmid DNA prepared by alkaline lysis (Bimboim, H. C. and Duly, J., Nuc. Acid Res., 1978 7:1513). A recombinant plasmid, containing the 20 kDa gene, was identified. DNA sequence was obtained from the clones using the Applied Biosystems PRISM Dye Terminator cycle-sequencing core kit based on the PRISM protocol supplied by the vendor. Approximately 1 ug of template DNA and 100 ng of primer were used for each cycling reaction. The reactions were cycled on the GeneAmp® PCR Systems 2400 unit, purified using the PRISM method, and analyzed on an ABI 373A DNA sequencer (Applied Biosystems).

The insert containing the r20 kDa gene was excised by restriction digestion with Nco1 and Sal1, and separated on a 1.5% Agarose gel. The DNA fragment was cut from the gel and purified away from the agarose by a Bio 101 SPIN kit (Vista, Calif.). The insert was ligated with plasmid vector DNA(pET28a) also digested with Nco1 and Sal1, and was subsequently transformed into Top 10F' cells (INVITROGEN). The kanamycin resistant transformants were screened by restriction digestion of plasmid DNA prepared by alkaline lysis (Bimboim, H. C. and Duly J., Nuc. Acid Res., 1978 7:1513). A recombinant plasmid was subsequently transformed into BL21 cells (Novagen) to create pLP533 and grown in SOB media supplemented with 30 ug/ml kanamycin. Cells were grown to an O.D.$_{600}$ of 0.6, and were subsequently induced with 0.4 mM IPTG (Boebringer Mannheim, Indianapolis, Ind.) for 2–4 hours. Whole cell lysates were prepared and electrophoresed on a 15% SDS-PAGE gel (Laemmli, U. K., Nature, 1970,227:680) to confirm expression of the desired recombinant product.

Purification of the Recombinant 20 kDa Surface Associated Protein.

A 250 mL flask containing 50 mL of SOB medium, supplemented with 30 µg/ML kanamycin (Sigma, St. Louis, Mo.), was inoculated with a scraping from a frozen culture of E. coli pLP533. The culture was incubated at 37° C. with shaking at 200 rpm for approximately 16 hours. Subsequently, two 1 liter flasks containing SOB plus 30 ug/ml kanamycin were inoculated with 20 mL of the overnight culture and incubated at 37° C. with shaking at 200 rpm. When the culture reached an optical density of OD$_{600}$0.7–0.8, IPTG (Gold Biotechnology, St. Louis, Mo.) was added to 0.8 mM. The culture was incubated at the same temperature with shaking for an additional three hours. The cells were then harvested by centrifugation for 15 mm. at 7300×g. The cell pellets were frozen at −20° C. and were then thawed and resuspended in 300 mL of 10 mM sodium phosphate pH 6.0 (J. T. Baker, Phillipsburg, Pa. ). The cell suspension was then passed through a microfluidizer (Microfluidics Corporation, Newton, Mass.) to lyse the cells. The lysate was centrifuged for 15 mm. at 16,000×g and the resulting supernatant was then centrifuged for 45 mm. at 200,000×g Supernatants and pellets at each step were assayed by SDS-PAGE. The supernatant was diluted to 500 mL in 10 mM sodium phosphate pH 6.0. The solution was then diafiltered with a 100,000 MW cutoff membrane (Millipore, Bedford, Mass.) against 1 L of the same buffer and concentrated 2.5 fold. The protein, in the retentate, was loaded onto a 70 mL ceramic hydroxyapatite column (BIO-RAD Laboratories Hercules, Calif.) in 10 mM sodium phosphate pH 6.0. The column was then washed with 10 column volumes (CV) of the loading buffer. Contaminating proteins were removed by washing the column with 10 CV of 108 mM sodium phosphate pH 6.0. The protein was eluted from the column with a linear gradient over 10 CV from 108 mM to 500 mM sodium phosphate pH 6.0. The peak fractions were run on a 10% –20% SDS-PAGE gel (Zaxis, Hudson, Ohio). The fractions containing the protein were pooled and stored at −20° C. The protein was analyzed for homogeneity by SDS-PAGE, and the concentration of protein during purification was determined by the method of Lowry (Lowry, O. H., et al, S. Biol. Chem., 1951, 198:265). Protein concentration prior to immunization was determined using a BCA kit obtained from Pierce Chemicals (Northbrook, Ill.) and was used according to the manufacturers directions. BSA was used as protein standard.

Polyclonal Antisera for Western Blot Analysis.

Recombinant protein was used to generate polyclonal antisera in mice. Briefly, 10 µg of r20 kDa protein was adjuvanted for each dose as an emulsion with Incomplete Freund's Adjuvant (IFA) (1:1v/v) and injected subcutaneously into 6–8 week old Swiss Webster mice. The mice were bled and vaccinated at wk 0, boosted at wk4, then exsanguinated at wk 6. Ten mice were vaccinated with the r20 kDa protein adjuvanted with IFA. The sera were pooled and used for further analysis.

SDS-PAGE and Western Blotting.

Whole cell lysates were prepared by centrifuging equivalent numbers of pneumococcal cells, based on the OD$_{600}$, in a microcentrifuge for 30 sec. Pneumococcal cell pellets were resuspended in an appropriate volume of loading buffer. Where indicated, samples were boiled for 5 mm and separated on a 10% SDS-PAGE gel using the method of Laemmli (Laemmli, Nature, 1970; 227:680). The samples were transferred to nitrocellulose (BioRad, Hercules, Calif.) using a BIO-RAD Mini Transblot cell (BIO-RAD) and the blots were blocked at room temp for 30 minutes in 5% nonfat milk-PBS (BLOTTO). Pooled mouse antisera were used at a 1:1000 dilution in BLOTTO for 60 minutes, followed by 25 minute washes in PBS-0.2% TWEEN 80. Goat anti-mouse IgG+M conjugated to alkaline phosphatase (Biosource International, Camarillo, Calif.) was used to detect bound antibodies at a 1:1000 dilution in BLOTTO. The blots were washed as previously described and detected with NBT and BCIP from BIO-RAD according to the manufacturer's directions.

Intranasal Immunization of Mice Prior to Challenge.

Six-week old, pathogen-free, Balb/c mice were purchased from Jackson Laboratories (Bar Harbor, Me.) and housed in cages under standard temperature, humidity, and lighting conditions. BALB/C mice, at 10 animals per group, were immunized with 5 µg of r20 kDa protein. On weeks 0, 2, and 4. On each occasion, 5 µg r20 kDa formulated with 0.1 µg of CT-E29H, a genetically modified cholera toxin that is reduced in enzymatic activity and toxicity (Tebbey, P. W., et al., Vaccine, 2000, 18:2723), was slowly instilled into the nostril of each mouse in a 10 µl volume. Mice immunized with Keyhole Limpet Hemocyanin (KLH)-CT-E29H were used as controls. Serum samples were collected 4 days after the last immunization.

Mouse Intranasal Challenge Model.

Balb/c mice were challenged on week 4 day 6 with $1\times10^5$ CFU's of serotype 3 streptomycin resistant S. pneumoniae. Pneumococci were inoculated into 3 ml of Todd-Hewitt broth containing 100 µg/ml of streptomycin. The culture was grown at 37° C. until mid-log phase, then diluted to the desired concentration with Todd-Hewitt broth and stored on ice until use. Each mouse was anesthetized with 1.2 mg of ketamine HCl (Fort Dodge Laboratory, Ft. Dodge, Iowa) by i.p. injection. The bacterial suspension was inoculated to the nostril of anesthetized mice (10 µl per mouse). The actual dose of bacteria administrated was confirmed by plate count. Four days after challenge, mice were sacrificed, the noses were removed, and homogenized in 3-ml sterile saline with a tissue homogenizer (Ultra-Turax T25, Janke & Kunkel Ika-Labortechnik, Staufen, Germany). The homogenate was 10-fold serially diluted in saline and plated on streptomycin containing TSA plates. Fifty µl of blood collected 2 days post-challenge from each mouse was also plated on the same kind of plates. Plates were incubated overnight at 37° C. and then colonies were counted.

ELISA Assay for r20 kDa Protein.

Antibody titers against r20 kDa protein were determined by enzyme-linked immunosorbent assay (ELISA). ELISAs were performed using r20 kDa (100 µl per well of a 5 µg/ml stock in PBS, pH7.1) to coat Nunc-Immuno™ PolySorp Plates. Plates were coated overnight at 4° C. After blocking with 200 µl of PBS containing 5% nonfat dry milk (blocking buffer) for 1 hour at room temperature, the plates were incubated with serial dilutions of test sera diluted in blocking buffer for 1.5 hours at room temperature. The plates were then washed five times with PBS containing 0.1% TWEEN (PBS-T) and incubated with biotinylated goat anti-mouse IgG or IgA (1:8000 or 1:4000 in PBS; Brookwood Biomedical, Birmingham, Ala.) for 1 hour at room temperature. After five additional washes with PBS-T, the plates were incubated with streptavidin conjugated horseradish peroxidase (1:10,000 in PBS; Zymed Laboratory Inc., San Francisco, Calif.) for 1 hour at room temperature. The plates were then washed five times with PBS-T, incubated 20 minutes with 100 µl of ABTS substrate (KPL, Gaithersburg, Md.), followed by addition of 100 µl stopping solution (1% SDS). Absorbance values were read at 405 nm using a VERSAmax microplate reader (Molecular Devices Corp., Sunnyvale, Calif.). The end point titers of test sera were the reciprocal of the highest mean dilution that resulted in an $OD_{405}$ reading of 0.1. The mean background titers of test sera were quantified by absorbance values read at 405 nm on the wells that had all reagents except sera.

Statistical Methods. Comparison of nasal colonization among groups was performed using the Tukey-Kramer test (Ludbrook, J., Clin Exp Pharmacol Physiol., 1998, 25:1032). Results were considered significant at $p<0.05$.

Sequence Heterogeneity of PPP1.

To examine sequence heterogeneity for the PPP1 protein, the nucleotide sequence for the gene was compared among 10 different serotypes. Genomic DNA was prepared from overnight cultures of each serotype of S. pneumoniae. Cells were harvested by centrifugation at 1000×g for 15 minutes at 4° C. and resuspended in 2 ml TE buffer. Cells were lysed by the addition of SDS to 0.3% and Proteinase K (SIGMA) to 10 µg/ml. The cells were incubated overnight at 55° C. Proteins were extracted from the cleared lysate by the addition of an equal volume of phenol/chloroform/isoamyl alcohol (made by combining a 24:1 mixture of chloroform/isoamyl alcohol with an equal volume of water saturated phenol). The phases were separated by centrifugation at 7500×g for 10 minutes at room temperature, then the aqueous phase was removed to a new tube. The process was repeated, then the DNA was precipitated from the aqueous phase by the addition of 10.4M $NH_4Ac$ to 20%, and 2.5 volume of ethanol. The genomic DNA was spooled out using a glass rod and resuspended in 200 µl TE buffer. The gene for PPP1 was sequenced from the genomic DNA of serotypes 1,3,4,5,6,7,9,14,18,23F, and CP1200, using the Applied Biosystems Prism Dye Terminator cycle-sequencing core kit based on the Prism protocol supplied by the vendor. Approximately 1 µg template DNA and 100 ng of primers were used for each cycling reaction. The reactions were cycled on the Gene Amp PCR Systems 2400 unit, purified using the Prism method, and analyzed on an ABI 373A DNA sequencer (Applied Biosystems). The nucleotide sequences and their predicted amino acid sequences were aligned in the Megalign application of the DNA LASER-GENE package from DNAstar, using the Clustal W algorithm.

Evaluation of PPP1 Message Expressed in vivo.

Preparation of RNA from Cells Grown in vitro

Various S. pneumoniae serotypes were grown to log phase ($O.D._{550}$ approx 0.3) in 60 ml THB –0.5%YE at 37° C. with 5% $CO_2$. The cells were harvested by centrifugation at 1000×g for 15 minutes at 4° C. The supernatant was aspirated and the cells were resuspended in 1 ml RNAse later (Ambion, Calif.) and stored for >1 hr at 4° C. The cells were then centrifuged in a microfuge for 5 minutes at 8000×g. The supernatant was aspirated and the cells were resuspended in 100 µl 10%Deoxycholate (DOC). 1100 µl of RNAZOL B (Tel-Test, Inc) was then added and the suspension mixed briefly by inversion. 120 µl of $CHCl_3$ were then added, the sample mixed by inversion and then centrifuged in a microfuge at full speed for 10 minutes at 4° C . The aqueous layer was removed and the RNA was precipitated by addition of an equal volume of 2-propanol. The RNA was incubated at 4° C. for >1 hr and then centrifuged in a microfuge at full speed for 10 minutes at room temperature. The supernatant was aspirated and the RNA was washed with 75% ethanol and recentrifuged for 5 minutes. The supernatant was aspirated and the RNA was resuspended in 50–100 µl nuclease free water. DNA was removed from the RNA by treating the sample with RNAse free DNAase (DNA FREE, Ambion) for 20 minutes at 37 degrees, followed by inactivation of the enzyme by addition of the DNA FREE chleator. The purity and yield of the RNA was assessed by measuring the absorbance at 260 and 280 nm.

Preparation of RNA from Cells Grown in vivo

Log phase S. pneumoniae cells were prepared as described above and resuspended to 106 cfu/ml in RPMI media (Celltech) supplemented with 0.4% glucose. 1 ml of the cell suspension was sealed in a PVDF dialysis membrane with a 80,000 MW cutoff (SprectraPor). Two such bags were implanted intraperitoneally in 400 g Sprague Dawley rats. The bags remained in the rats for 22 hours, after which the rats were terminated and the bags were harvested. RNA was prepared from the intraperitoneally grown cells as described above.

RT-PCR to Examine the Message for PPP1 in vivo

Message for the PPP1 gene was amplified out from both RNA prepared from in vitro and in vivo grown cells using RT-PCR. A reverse PCR primer corresponding to the 3' end of the gene was used to generate ds cDNA in the following reaction. 1 µg RNA was incubated with 0.25 µM of the reverse primer: GGG GTC GAC TAA ACC AGG TGC TTG TCC AAG TTC (SEQ ID NO:8) for 3 minutes at 75° C., then cooled to 44° C. The message was reverse transcribed using the RETROscript (Ambion) kit according to the manufacturer's directions. ReddyMix (ABgene) was used according to the manufacturer's directions to amplify the PPP1 message from 2–5 µl of the sample, using 0.25 µM of the above reverse primer and the forward primer: GGG GCC ATG GCT GTA GAA TTG AAA AAA GAA (SEQ ID NO:9). 10 µl of the amplified product was electrophoresed on a 2% Agarose gel.

Results

Figure 2:
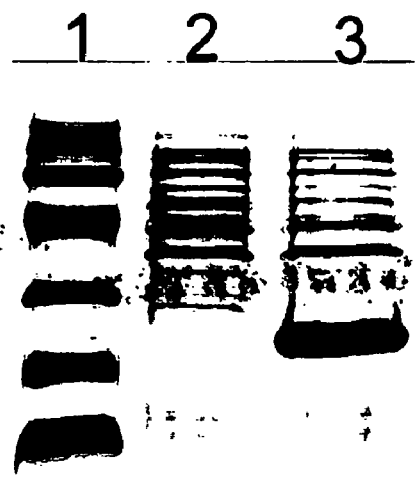
FIG. 2. Gel of whole cell lysate of recombinant expression of pLP533 showing expression of the desired product. Lane 1, Biorad prestained markers; Lane 2, uninduced cells; Lane 3, induced cells.

Identification of the 20 kDa surface associated protein—A PBS wash and ion exchange chromatography was used to identify an 20 kDa surface associated component of S. pneumoniae (FIG. 1). Lane 2–9 in FIG. 1 represents fraction #8–16 from a DEAE column. There is clearly a major protein band between 15 and 20 kDa. The low molecular weight band was resolved on a preparative SDS-PAGE gel and transferred to a PVDF membrane. The PVDF membrane has a high binding capacity, which increases sample recovery and sequencing performance, allowing efficient determination of the amino terminal residues. The amino terminal sequence (SEQ ID NO: 3) of this protein allowed the identification of a corresponding open reading frame in the S. pneumoniae genome (SEQ ID NOS: 4 and 5). This ORF showed similarity to similar to non-heme iron-containing ferritin proteins in other organisms, which may indicate similar function in S. pneumoniae (Pikis, A., et al., J. Infectious Diseases, 1998, 178:700). However, the exact function and cellular location of the proteins in S. pneumoniae is unknown. Subcloning and expression of this ORF provided recombinant material of the expected size (FIG. 2).

Figure 5:
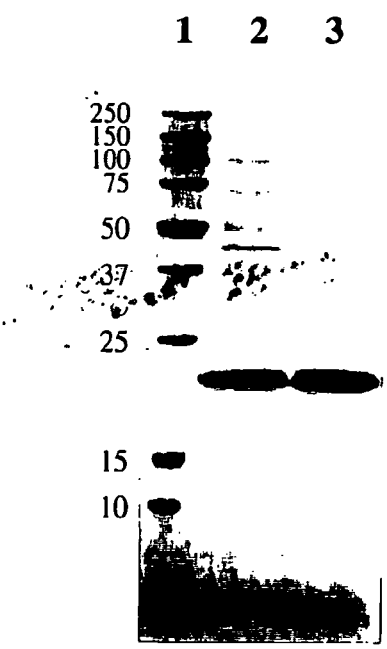
FIG. 5. SDS-PAGE gel shows purification of rPPP1. Lane 1, Bio Rad Precision standards; lane 2, diafiltrate; lane 3, purified rPPP1.

Purification of the recombinant 20 kDa surface associated protein. Purification was aided by the solubility of the recombinant protein. Significant purification away from cellular membranes was achieved by sequential centrifugations. In addition, the characteristic oligomer formation was successfully utilized to remove the remaining low molecular weight contaminating proteins by diafiltration. The predicted charge of the protein at neutral pH allowed the protein to be purified to greater than 90% homogeneity on a Hydroxyapatite column, as seen in FIG. 5.

Figure 3:
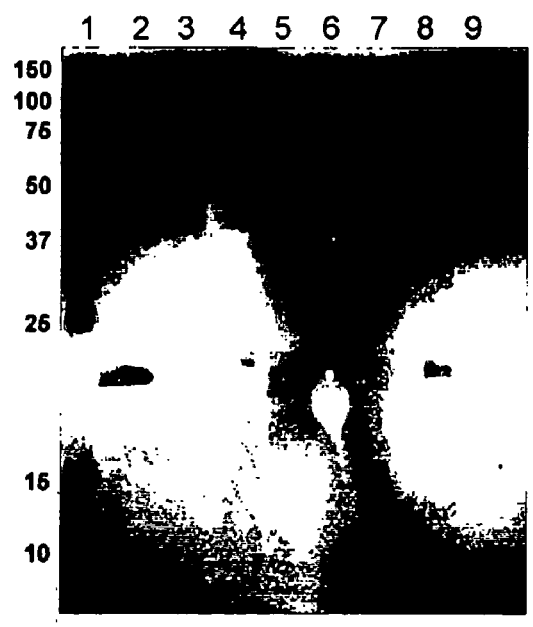
FIG. 3. Western blot of whole cell lysates of several serotypes showing cross reactivity and oligomer formation. Lane 1, Biorad Precision prestained markers; lane 2, type 3; lane 3, type 4; lane 4, type 9; lane 5, type 14; lane 6, type 19F; lane 7, type 18C; lane 8, type 5; and lane 9, tupe 23F.

Reactivity of anti-r20 kDa surface associated protein sera. Polyclonal antisera to recombinant 20 kDa surface associated protein were generated in Swiss Webster mice to evaluate antigenic conservation of the protein among strains. Antisera to the r20 kDa protein reacted with proteins of approximately 20, 40, and 80 kDa in unheated whole cell lysates of native species (FIG. 3), while the major reactive species seen in heated samples is at approximately 20 kDa (not shown). These results suggest that this protein is part of a complex of 4 subunits or more.

Figure 4:
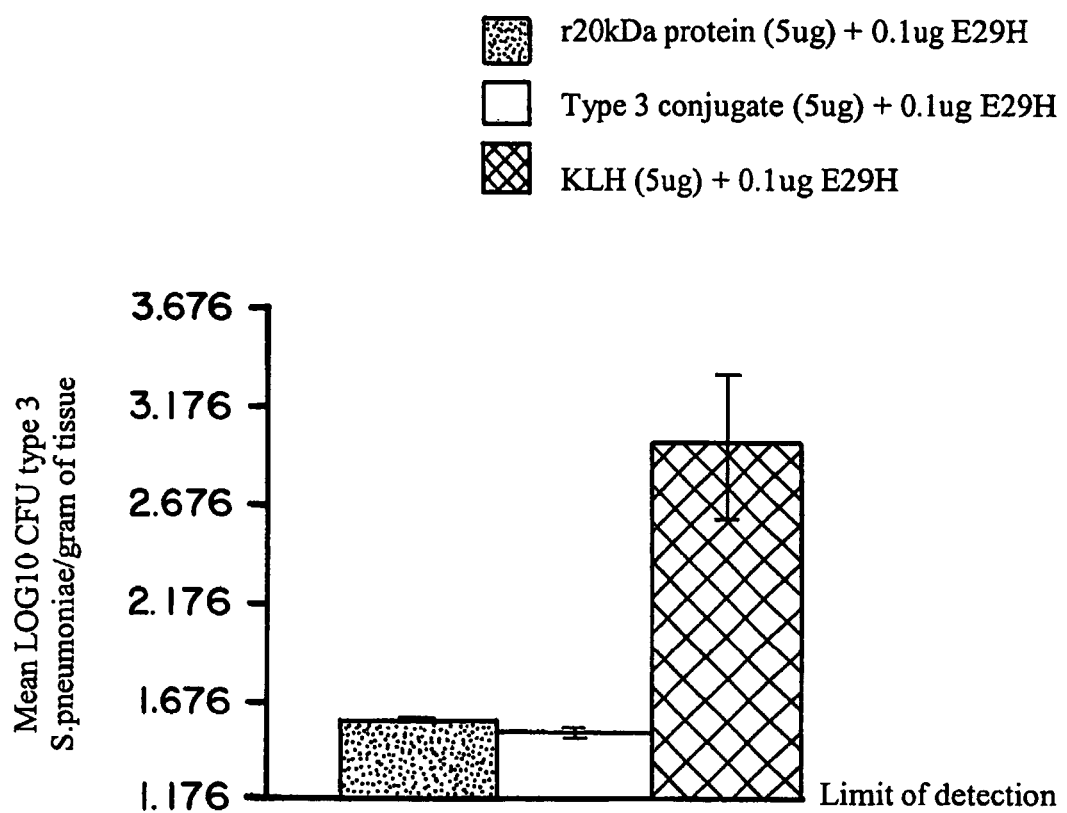
FIG. 4. Reduction of colonization by rPPP1. Bacteria recovered shown as Log10 CFU/gram of tissue. One standard error of the mean is shown. *values are significantly different compared to the control by Tukey-Kramer statistical test.

Intranasal Challenge. To determine whether i.n. immunization with r20 kDa surface associated protein can induce serum immune responses, Balb/c mice were administered 5 µg r20 kDa 3 times at biweekly intervals using CT-E29H (0.1 µg/dose) as a mucosal adjuvant. Immune sera collected 4 days after the last booster immunization were tested in the antigen-specific ELISA assays. At 4 days after the last booster immunization, strong, antigen-specific IgG and IgA antibody responses were generated in mice immunized with r20 kDa- E29H (Table 6). When compared to the unrelated protein KLH, immunization with r20 kDa surface associated protein was able to significantly reduce colonization of type 3 S. pneumoniae the nasopharynx of BALB/C mice. (FIG. 4) The results are comparable to the ability of the type 3 conjugate to reduce colonization of the homologous serotype (Henrikson, J, et al. Alcohol Clin Exp Res, 1997, 21:1630).

Antigen specific ELISA titers for r20kDa surface associated protein from S. pneumoniae.

| Group | Sera wk4d5 IgG | Sera wk4d5 IgA |
|---|---|---|
| 5 µg r20kDa + 0.1 ug CT-E29H | 79,726 | 1563 |
| 5 µg Type-3-Conjugate + 0.1 ug CT-E29H | <50 | <50 |
| 5 µg KLH + 0.1 ug CT-E29H | <50 | <50 |

Note:
Endpoint titers determined from pools of 5 BALB/c mice

Sequence Alignment of the PPP1 protein from 10 serotypes. As shown in FIG. 6, the sequence of PPP1 is largely conserved among serotypes. As can be seen, serotype 9 is the most divergent serotype. The PP1 isolated from this serotype showed 15 amino acid differences from the majority. The remaining serotypes showed less than 5 amino acid differences. An overall consensus sequence of PPP1 is shown in FIG. 6 (SEQ ID NO:20).

Figure 7:
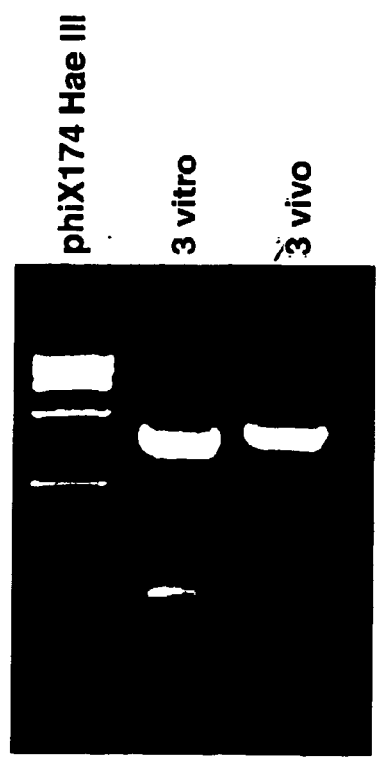
FIG. 7. Gel shows amplified PPP1 from in vitro and in vivo cultures.

RNA Amplification. A discrete band of the expected size is seen in both the in vitro and in vivo samples (FIG. 7). The size of the product was estimated to be full length by comparison to Hae III restriction fragments of Lambda DNA.

The patents, applications, test methods, and publications mentioned herein are hereby incorporated by reference in their entireties.

Many variations of the present invention will suggest themselves to those skilled in the art in light of the above detailed description. All such obvious variations are within the full intended scope of the appended claims.

We claim:

1. An immunogenic composition comprising an isolated *Streptococcus pneumoniae* Pneumo Protective Protein (PPP) comprising the amino acid sequence of SEQ ID NO: 5, wherein the PPP has a molecular weight of about 20 kDa and the ability to reduce colonization of pneumococcal bacteria.

2. The immunogenic composition of claim 1 and a pharmaceutically acceptable carrier.

3. The immunogenic composition of claim 1, wherein said PPP has an isoelectric point of about 4.587.

4. The immunogenic composition of claim 1, wherein said PPP has a charge of about −14.214 at pH 7.

5. The immunogenic composition of claim 2, wherein the composition further comprises at least one adjuvant.

6. The immunogenic composition of claim 1, wherein the PPP is a recombinant protein.

7. The immunogenic composition of claim 1, wherein the PPP is isolated from *S. pneumoniae*.

8. The immunogenic composition of claim 1, further comprising additional *S. pneumoniae* antigens.

9. A method of inducing an immune response in a mammal to *Streptococcus pneumoniae* PPP, said method comprising administering to said mammal an amount of the immunogenic composition of claim 1 effective to induce said immune response in said mammal.

* * * * *

SEQUENCE LISTING

<160> NUMBER OF SEQ ID NOS: 20

<210> SEQ ID NO 1
<211> LENGTH: 30
<212> TYPE: DNA
<213> ORGANISM: Artificial Sequence
<220> FEATURE:
<223> OTHER INFORMATION: 5' primer

<400> SEQUENCE: 1
ggggccatgg tctttccagt ttggtcaaaa        30

<210> SEQ ID NO 2
<211> LENGTH: 36
<212> TYPE: DNA
<213> ORGANISM: Artificial Sequence
<220> FEATURE:
<223> OTHER INFORMATION: 3' primer

<400> SEQUENCE: 2
ggggtcgact tataaaccag gtgcttgtcc aagttc        36

<210> SEQ ID NO 3
<211> LENGTH: 20
<212> TYPE: PRT
<213> ORGANISM: Streptococcus pneumoniae

<400> SEQUENCE: 3

Val Glu Leu Lys Lys Glu Ala Val Lys Asp Val Thr Ser Leu Thr Lys
1               5                   10                  15

Ala Ala Pro Val
            20

<210> SEQ ID NO 4
<211> LENGTH: 537
<212> TYPE: DNA
<213> ORGANISM: Streptococcus pneumoniae

<400> SEQUENCE: 4
atgaatgagg taagaaaaat ggtagaattg aaaaaagaag cagtaaaaga cgtaacatca        60
ttgacaaaag cagcgccagt agcattggca aaaacaaagg aagtcttgaa ccaagctgtt       120
gctgatttgt atgtagctca cgttgctttg caccaagtgc actggtatat gcatggtcgt       180
ggtttccttg tatggcatcc aaaaatggat gagtacatga agctcttga cggtcaattg       240 gatgaaatca gtgaacgctt gattacactc ggtggaagcc cattctctac attgacagag       300
ttccttcaaa atagtgaaat cgaagaagaa gctggtgaat accgtaatgt tgaagaaagc       360
ttggaacgtg ttcttgttat ctaccgttac ttgtcagaac ttttccaaaa aggtttggat       420
gtcactgatg aagaaggtga cgatgtgaca acggtatct ttgcaggcgc taaaactgaa       480
acagataaaa caatttggat gcttgcagcc gaacttggac aagcacctgg tttgtaa          537

<210> SEQ ID NO 5
<211> LENGTH: 178
<212> TYPE: PRT
<213> ORGANISM: Streptococcus pneumoniae

<400> SEQUENCE: 5

Met Asn Glu Val Lys Lys Met Val Glu Leu Lys Lys Glu Ala Val Lys
1               5                   10                  15

-continued

Asp Val Thr Ser Leu Thr Lys Ala Ala Pro Val Ala Leu Ala Lys Thr
                20                  25                  30

Lys Glu Val Leu Asn Gln Ala Val Ala Asp Leu Tyr Val Ala His Val
            35                  40                  45

Ala Leu His Gln Val His Trp Tyr Met His Gly Arg Gly Phe Leu Val
 50                  55                  60

Trp His Pro Lys Met Asp Glu Tyr Met Glu Ala Leu Asp Gly Gln Leu
 65                  70                  75                  80

Asp Glu Ile Ser Glu Arg Leu Ile Thr Leu Gly Gly Ser Pro Phe Ser
                85                  90                  95

Thr Leu Thr Glu Phe Leu Gln Asn Ser Glu Ile Glu Glu Ala Gly
            100                 105                 110

Glu Tyr Arg Asn Val Glu Glu Ser Leu Glu Arg Val Leu Val Ile Tyr
        115                 120                 125

Arg Tyr Leu Ser Glu Leu Phe Gln Lys Gly Leu Asp Val Thr Asp Glu
130                 135                 140

Glu Gly Asp Asp Val Thr Asn Gly Ile Phe Ala Gly Ala Lys Thr Glu
145                 150                 155                 160

Thr Asp Lys Thr Ile Trp Met Leu Ala Ala Glu Leu Gly Gln Ala Pro
                165                 170                 175

Gly Leu

<210> SEQ ID NO 6
<211> LENGTH: 42
<212> TYPE: PRT
<213> ORGANISM: Homo sapiens

<400> SEQUENCE: 6

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 7
<211> LENGTH: 28
<212> TYPE: PRT
<213> ORGANISM: Homo sapiens

<400> SEQUENCE: 7

Asp Ala Glu Phe Arg His Asp Ser Gly Tyr Glu Val His His Gln Lys
 1               5                  10                  15

Leu Val Phe Phe Ala Glu Asp Val Gly Ser Asn Lys
            20                  25

<210> SEQ ID NO 8
<211> LENGTH: 33
<212> TYPE: DNA
<213> ORGANISM: Artificial Sequence
<220> FEATURE:
<223> OTHER INFORMATION: Reverse primer

<400> SEQUENCE: 8
ggggtcgact aaaccaggtg cttgtccaag ttc                           33

<210> SEQ ID NO 9
<211> LENGTH: 30
<212> TYPE: DNA

-continued

<213> ORGANISM: Artificial Sequence
<220> FEATURE:
<223> OTHER INFORMATION: Forward primer

<400> SEQUENCE: 9
ggggccatgg ctgtagaatt gaaaaaagaa                    30

<210> SEQ ID NO 10
<211> LENGTH: 176
<212> TYPE: PRT
<213> ORGANISM: Streptococcus pneumoniae

<400> SEQUENCE: 10

Met Ala Val Glu Leu Lys Lys Glu Ala Val Lys Asp Val Thr Ser Leu
1               5                   10                  15

Thr Lys Ala Ala Pro Val Ala Leu Ala Lys Thr Lys Glu Val Leu Asn
            20                  25                  30

Gln Ala Val Ala Asp Leu Tyr Val Ala His Val Ala Leu His Gln Val
        35                  40                  45

His Trp Tyr Met His Gly Arg Gly Phe Leu Val Trp His Pro Lys Met
    50                  55                  60

Asp Glu Tyr Met Glu Ala Leu Asp Gly Gln Leu Asp Glu Ile Ser Glu
65                  70                  75                  80

Arg Leu Ile Thr Leu Gly Gly Ser Pro Phe Ser Thr Leu Thr Glu Phe
                85                  90                  95

Leu Gln Asn Ser Glu Ile Glu Glu Ala Gly Glu Tyr Arg Asn Val
            100                 105                 110

Glu Glu Ser Leu Glu Arg Val Leu Val Ile Tyr Arg Tyr Leu Ser Glu
        115                 120                 125

Leu Phe Gln Lys Gly Leu Asp Val Thr Asp Glu Gly Asp Asp Val
    130                 135                 140

Thr Asn Gly Ile Phe Ala Gly Ala Lys Thr Glu Thr Asp Lys Thr Ile
145                 150                 155                 160

Trp Met Leu Ala Ala Glu Leu Gly Gln Ala Pro Gly Leu Val Asp Pro
                165                 170                 175

<210> SEQ ID NO 11
<211> LENGTH: 176
<212> TYPE: PRT
<213> ORGANISM: Streptococcus pneumoniae

<400> SEQUENCE: 11

Met Ala Val Glu Leu Lys Lys Glu Ala Val Lys Asp Val Thr Ser Leu
1               5                   10                  15

Thr Lys Ala Ala Pro Val Ala Leu Ala Lys Thr Lys Glu Val Leu Asn
            20                  25                  30

Gln Ala Val Ala Asp Leu Tyr Val Ala His Val Ala Leu His Gln Val
        35                  40                  45

His Trp Tyr Met His Gly Arg Gly Phe Leu Val Trp His Pro Lys Met
    50                  55                  60

Asp Glu Tyr Met Glu Ala Leu Asp Gly Gln Leu Asp Glu Ile Ser Glu
65                  70                  75                  80

Arg Leu Ile Thr Leu Gly Gly Ser Pro Phe Ser Thr Leu Thr Glu Phe
                85                  90                  95

Leu Gln Asn Ser Glu Ile Glu Glu Ala Gly Glu Tyr Arg Asn Val
            100                 105                 110

Glu Glu Ser Leu Glu Arg Val Leu Val Ile Tyr Arg Tyr Leu Ser Glu

```
                    115                 120                 125
Leu Phe Gln Lys Gly Leu Asp Val Thr Asp Glu Glu Gly Asp Asp Val
            130                 135                 140

Thr Asn Gly Ile Phe Ala Gly Ala Lys Thr Glu Thr Asp Lys Thr Ile
145                 150                 155                 160

Trp Met Leu Ala Ala Glu Leu Gly Gln Ala Pro Gly Leu Val Asp Pro
                165                 170                 175

<210> SEQ ID NO 12
<211> LENGTH: 176
<212> TYPE: PRT
<213> ORGANISM: Streptococcus pneumoniae

<400> SEQUENCE: 12

Met Ala Val Glu Leu Lys Lys Glu Ala Val Lys Asp Val Thr Ser Leu
1               5                   10                  15

Thr Lys Ala Ala Pro Val Ala Leu Ala Lys Thr Lys Glu Val Leu Asn
            20                  25                  30

Gln Ala Val Ala Asp Leu Tyr Val Ala His Val Ala Leu His Gln Val
        35                  40                  45

His Trp Tyr Met His Gly Arg Gly Phe Leu Val Trp His Pro Lys Met
    50                  55                  60

Asp Glu Tyr Met Glu Ala Leu Asp Gly Gln Leu Asp Glu Ile Ser Glu
65                  70                  75                  80

Arg Leu Ile Thr Leu Gly Gly Ser Pro Phe Ser Thr Leu Thr Glu Phe
                85                  90                  95

Leu Gln Asn Ser Glu Ile Glu Glu Ala Gly Glu Tyr Arg Asn Val
            100                 105                 110

Glu Glu Ser Leu Glu Arg Val Leu Val Ile Tyr Arg Tyr Leu Ser Glu
        115                 120                 125

Leu Phe Gln Lys Gly Leu Asp Val Thr Asp Glu Glu Gly Asp Asp Val
            130                 135                 140

Thr Asn Gly Ile Phe Glu Gly Ala Lys Thr Glu Thr Asp Lys Thr Ile
145                 150                 155                 160

Trp Met Leu Ala Ala Glu Leu Gly Gln Ala Pro Gly Leu Val Asp Pro
                165                 170                 175

<210> SEQ ID NO 13
<211> LENGTH: 175
<212> TYPE: PRT
<213> ORGANISM: Streptococcus pneumoniae

<400> SEQUENCE: 13

Ala Val Glu Leu Lys Lys Glu Ala Val Lys Asp Val Thr Ser Leu Thr
1               5                   10                  15

Lys Ala Ala Pro Val Ala Leu Ala Lys Thr Lys Glu Val Leu Asn Gln
            20                  25                  30

Ala Val Ala Asp Leu His Val Ala His Val Ala Leu His Gln Val His
        35                  40                  45

Trp Tyr Met His Gly Arg Gly Phe Leu Val Trp His Pro Lys Met Asp
    50                  55                  60

Glu Tyr Met Glu Ala Leu Asp Gly Gln Leu Asp Glu Thr Ser Glu Arg
65                  70                  75                  80

Leu Ile Thr Leu Gly Gly Ser Pro Phe Ser Thr Leu Thr Glu Phe Leu
                85                  90                  95

Gln Asn Ser Glu Ile Glu Glu Glu Ala Gly Glu Tyr Arg Asn Val Glu
```

```
            100                 105                 110
Glu Ser Leu Glu Arg Val Leu Val Ile Tyr Arg Tyr Leu Ser Glu Leu
            115                 120                 125

Phe Gln Lys Asp Leu Asp Val Thr Asp Glu Glu Gly Asp Asp Val Thr
        130                 135                 140

Asn Gly Ile Phe Ala Gly Ala Lys Thr Glu Thr Asp Lys Thr Ile Trp
145                 150                 155                 160

Met Leu Ala Ala Glu Leu Gly Gln Ala Pro Gly Leu Val Asp Pro
                165                 170                 175

<210> SEQ ID NO 14
<211> LENGTH: 176
<212> TYPE: PRT
<213> ORGANISM: Streptococcus pneumoniae

<400> SEQUENCE: 14

Met Ala Val Glu Leu Lys Lys Glu Ala Val Lys Asp Val Thr Ser Leu
1               5                   10                  15

Thr Lys Ala Ala Pro Val Ala Leu Ala Lys Thr Lys Glu Val Leu Asn
            20                  25                  30

Gln Ala Val Ala Asp Leu Tyr Val Ala His Val Ala Leu His Gln Val
        35                  40                  45

His Trp Tyr Met His Gly Arg Gly Phe Leu Val Trp His Pro Lys Met
    50                  55                  60

Asp Glu Tyr Met Glu Ala Leu Asp Gly Gln Leu Asp Glu Ile Ser Glu
65                  70                  75                  80

Arg Leu Ile Thr Leu Gly Gly Ser Pro Phe Ser Thr Leu Thr Glu Phe
                85                  90                  95

Leu Gln Asn Ser Glu Ile Glu Glu Ala Gly Glu Tyr Arg Asn Val
            100                 105                 110

Glu Glu Ser Leu Glu Arg Val Leu Val Ile Tyr Arg Tyr Leu Ser Glu
        115                 120                 125

Leu Phe Gln Lys Gly Leu Asp Val Thr Asp Glu Glu Gly Asp Asp Val
    130                 135                 140

Thr Asn Asp Ile Phe Val Gly Ala Lys Thr Glu Thr Asp Lys Thr Ile
145                 150                 155                 160

Trp Met Leu Ala Ala Glu Leu Gly Gln Ala Pro Gly Leu Val Asp Pro
                165                 170                 175

<210> SEQ ID NO 15
<211> LENGTH: 176
<212> TYPE: PRT
<213> ORGANISM: Streptococcus pneumoniae

<400> SEQUENCE: 15

Met Ala Val Glu Leu Lys Lys Glu Ala Val Lys Asp Val Thr Ser Leu
1               5                   10                  15

Thr Lys Ala Ala Pro Val Ala Leu Ala Lys Thr Lys Glu Val Leu Asn
            20                  25                  30

Gln Ala Val Ala Asp Leu Tyr Val Ala His Val Ala Leu His Gln Val
        35                  40                  45

His Trp Tyr Met His Gly Arg Gly Phe Leu Val Trp His Pro Lys Met
    50                  55                  60

Asp Glu Tyr Met Glu Ala Leu Asp Gly Gln Leu Asp Glu Ile Ser Glu
65                  70                  75                  80

Arg Leu Ile Thr Leu Gly Gly Ser Pro Phe Ser Thr Leu Thr Glu Phe
```

-continued

```
                85                  90                  95
Leu Gln Asn Ser Glu Ile Glu Glu Ala Gly Glu Tyr Arg Asn Val
            100                 105                 110
Glu Glu Ser Leu Glu Arg Val Leu Val Ile Tyr Arg Tyr Leu Ser Glu
            115                 120                 125
Leu Phe Gln Lys Gly Leu Asp Val Thr Asp Glu Gly Asp Asp Val
            130                 135                 140
Thr Asn Gly Ile Phe Ala Gly Ala Lys Thr Glu Thr Asp Lys Thr Ile
145                 150                 155                 160
Trp Met Leu Ala Ala Glu Leu Gly Gln Ala Pro Gly Leu Val Asp Pro
                165                 170                 175

<210> SEQ ID NO 16
<211> LENGTH: 176
<212> TYPE: PRT
<213> ORGANISM: Streptococcus pneumoniae

<400> SEQUENCE: 16

Met Ala Val Glu Leu Lys Lys Glu Ala Val Lys Asp Val Thr Ser Leu
1               5                   10                  15
Thr Lys Ala Ala Pro Val Ala Leu Ala Lys Thr Lys Glu Val Leu Asn
            20                  25                  30
Gln Ala Val Ala Asp Leu Tyr Val Ala His Val Ala Leu His Gln Val
        35                  40                  45
His Trp Tyr Met His Gly Arg Gly Phe Leu Val Trp His Pro Lys Met
    50                  55                  60
Asp Glu Tyr Met Glu Ala Leu Asp Gly Gln Leu Asp Glu Ile Ser Glu
65                  70                  75                  80
Arg Leu Ile Thr Leu Gly Gly Ser Pro Phe Ser Thr Leu Thr Glu Phe
                85                  90                  95
Leu Gln Asn Ser Glu Ile Glu Glu Ala Gly Glu Tyr Arg Asn Val
            100                 105                 110
Glu Glu Ser Leu Glu Arg Val Leu Val Ile Tyr Arg Tyr Leu Ser Glu
            115                 120                 125
Leu Phe Gln Lys Gly Leu Asp Val Thr Asp Glu Gly Asp Asp Val
            130                 135                 140
Thr Asn Asp Ile Phe Val Gly Ala Lys Thr Glu Thr Asp Lys Thr Ile
145                 150                 155                 160
Trp Met Leu Ala Ala Glu Leu Gly Gln Ala Pro Gly Leu Val Asp Pro
                165                 170                 175

<210> SEQ ID NO 17
<211> LENGTH: 176
<212> TYPE: PRT
<213> ORGANISM: Streptococcus pneumoniae

<400> SEQUENCE: 17

Met Ala Val Glu Leu Lys Lys Glu Ala Val Lys Asp Val Thr Ser Leu
1               5                   10                  15
Thr Lys Ala Ala Pro Val Ala Leu Ala Lys Thr Lys Glu Val Leu Asn
            20                  25                  30
Gln Ala Val Ala Asp Leu Tyr Val Ala His Val Ala Leu His Gln Val
        35                  40                  45
His Trp Tyr Met His Gly Arg Gly Phe Leu Val Trp His Pro Lys Met
    50                  55                  60
Asp Glu Tyr Met Glu Ala Leu Asp Gly Gln Leu Asp Glu Ile Ser Glu
```

```
                65                  70                  75                  80
Arg Leu Ile Thr Leu Gly Gly Ser Phe Ser Thr Leu Thr Glu Phe
                    85                  90                  95

Leu Gln Asn Ser Glu Ile Glu Glu Ala Gly Glu Tyr Arg Asn Val
                100                 105                 110

Glu Glu Ser Leu Glu Arg Val Leu Val Ile Tyr Arg Tyr Leu Ser Glu
                115                 120                 125

Leu Phe Gln Lys Gly Leu Asp Val Thr Asp Glu Glu Gly Asp Asp Val
                130                 135                 140

Thr Asn Gly Ile Phe Ala Gly Ala Lys Thr Glu Thr Asp Lys Thr Ile
145                 150                 155                 160

Trp Met Leu Ala Ala Glu Leu Gly Gln Ala Pro Gly Leu Val Asp Pro
                165                 170                 175

<210> SEQ ID NO 18
<211> LENGTH: 176
<212> TYPE: PRT
<213> ORGANISM: Streptococcus pneumoniae

<400> SEQUENCE: 18

Met Ala Val Glu Leu Lys Lys Glu Ala Val Lys Asp Val Thr Ser Leu
1               5                   10                  15

Thr Lys Ala Ala Pro Val Ala Leu Ala Lys Thr Lys Glu Val Leu Asn
                20                  25                  30

Gln Ala Val Ala Asp Leu Tyr Val Ala His Val Ala Leu His Gln Val
                35                  40                  45

His Trp Tyr Met His Gly Arg Gly Phe Leu Val Trp His Pro Lys Met
            50                  55                  60

Asp Glu Tyr Met Glu Ala Leu Asp Gly Gln Leu Asp Glu Ile Ser Glu
65                  70                  75                  80

Arg Leu Ile Thr Leu Gly Gly Ser Pro Phe Ser Thr Leu Thr Glu Phe
                85                  90                  95

Leu Gln Asn Ser Glu Ile Glu Glu Ala Gly Glu Tyr Arg Asn Val
                100                 105                 110

Glu Glu Ser Leu Glu Arg Val Leu Val Ile Tyr Arg Tyr Leu Ser Glu
                115                 120                 125

Leu Phe Gln Lys Gly Leu Asp Val Thr Asp Glu Glu Gly Asp Asp Val
                130                 135                 140

Thr Asn Gly Ile Phe Ala Gly Ala Lys Thr Glu Thr Asp Lys Thr Ile
145                 150                 155                 160

Trp Met Leu Ala Ala Glu Leu Gly Gln Ala Pro Gly Leu Val Asp Pro
                165                 170                 175

<210> SEQ ID NO 19
<211> LENGTH: 176
<212> TYPE: PRT
<213> ORGANISM: Streptococcus pneumoniae

<400> SEQUENCE: 19

Met Ala Val Glu Leu Lys Lys Glu Ala Ala Lys Asp Val Ala Arg Leu
1               5                   10                  15

Thr Lys Ala Ala Pro Val Ala Leu Ala Lys Thr Lys Glu Val Leu Asn
                20                  25                  30

Gln Ala Val Ala Asp Leu Tyr Val Ala His Val Ala Leu His Gln Val
                35                  40                  45

His Trp Tyr Met His Gly Arg Gly Phe Leu Val Trp His Pro Lys Met
```

-continued

```
                50                  55                  60
Asp Glu Tyr Met Glu Ala Leu Asp Gly His Leu Asp Glu Ile Ser Glu
 65                  70                  75                  80

Arg Leu Ile Thr Leu Gly Gly Ser Pro Phe Ser Thr Leu Thr Glu Phe
                    85                  90                  95

Leu Gln Asn Ser Glu Ile Glu Glu Ala Gly Glu Tyr Arg Asn Val
                100                 105                 110

Glu Glu Ser Leu Glu Arg Val Leu Ala Ile Tyr Arg Tyr Leu Ile Thr
                115                 120                 125

Leu Phe Gln Lys Ala Leu Asp Val Thr Asp Glu Glu Gly Asp Asp Val
                130                 135                 140

Thr Asn Asp Ile Phe Val Gly Ala Lys Ala Glu Leu Glu Lys Thr Val
145                 150                 155                 160

Trp Met Leu Ala Ala Glu Leu Gly Gln Ala Pro Gly Leu Val Asp Pro
                    165                 170                 175
```

<210> SEQ ID NO 20
<211> LENGTH: 176
<212> TYPE: PRT
<213> ORGANISM: Artificial Sequence
<220> FEATURE:
<223> OTHER INFORMATION: Consensus sequence

<400> SEQUENCE: 20

```
Met Ala Val Glu Leu Lys Lys Glu Ala Val Lys Asp Val Thr Ser Leu
  1               5                  10                  15

Thr Lys Ala Ala Pro Val Ala Leu Ala Lys Thr Lys Glu Val Leu Asn
                    20                  25                  30

Gln Ala Val Ala Asp Leu Tyr Val Ala His Val Ala Leu His Gln Val
                    35                  40                  45

His Trp Tyr Met His Gly Arg Gly Phe Leu Val Trp His Pro Lys Met
 50                  55                  60

Asp Glu Tyr Met Glu Ala Leu Asp Gly Gln Leu Asp Glu Ile Ser Glu
 65                  70                  75                  80

Arg Leu Ile Thr Leu Gly Gly Ser Pro Phe Ser Thr Leu Thr Glu Phe
                    85                  90                  95

Leu Gln Asn Ser Glu Ile Glu Glu Ala Gly Glu Tyr Arg Asn Val
                100                 105                 110

Glu Glu Ser Leu Glu Arg Val Leu Val Ile Tyr Arg Tyr Leu Ser Glu
                115                 120                 125

Leu Phe Gln Lys Gly Leu Asp Val Thr Asp Glu Glu Gly Asp Asp Val
                130                 135                 140

Thr Asn Gly Ile Phe Ala Gly Ala Lys Thr Glu Thr Asp Lys Thr Ile
145                 150                 155                 160

Trp Met Leu Ala Ala Glu Leu Gly Gln Ala Pro Gly Leu Val Asp Pro
                    165                 170                 175
```